(12) United States Patent
Ikeda et al.

(10) Patent No.: US 11,260,000 B2
(45) Date of Patent: Mar. 1, 2022

(54) COMPOSITION IN THE FORM OF NANO OR MICRO EMULSION OR WITH LAMELLAR STRUCTURE

(71) Applicant: L'OREAL, Paris (FR)

(72) Inventors: Yuichi Ikeda, Kawasaki (JP); Maki Koide, Kawasaki (JP); Anne-Laure Bernard, Clark, NJ (US); Chantal Jouy, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/312,432

(22) PCT Filed: Jun. 10, 2015

(86) PCT No.: PCT/JP2015/067379
§ 371 (c)(1),
(2) Date: Nov. 18, 2016

(87) PCT Pub. No.: WO2015/198922
PCT Pub. Date: Dec. 30, 2015

(65) Prior Publication Data
US 2017/0087064 A1    Mar. 30, 2017

(30) Foreign Application Priority Data

Jun. 25, 2014 (JP) .............................. JP2014-130219

(51) Int. Cl.
| | | |
|---|---|---|
| *A61K 8/06* | (2006.01) | |
| *A61K 8/34* | (2006.01) | |
| *A61K 8/39* | (2006.01) | |
| *A61K 8/02* | (2006.01) | |
| *A61Q 19/02* | (2006.01) | |
| *A61K 8/92* | (2006.01) | |
| *A61Q 19/00* | (2006.01) | |

(52) U.S. Cl.
CPC ............ *A61K 8/068* (2013.01); *A61K 8/0295* (2013.01); *A61K 8/06* (2013.01); *A61K 8/347* (2013.01); *A61K 8/39* (2013.01); *A61K 8/92* (2013.01); *A61Q 19/00* (2013.01); *A61Q 19/02* (2013.01); *A61K 2800/21* (2013.01); *A61K 2800/262* (2013.01)

(58) Field of Classification Search
CPC ........ A61K 8/068; A61K 8/92; A61K 8/0295; A61K 8/39; A61K 8/347
See application file for complete search history.

(56) References Cited

U.S. PATENT DOCUMENTS

| | | | |
|---|---|---|---|
| 2,528,378 A | 10/1950 | Mannheimer | |
| 2,781,354 A | 2/1957 | Mannheimer | |
| 5,364,633 A | 11/1994 | Hill et al. | |
| 5,411,744 A | 5/1995 | Hill et al. | |
| 5,618,523 A | 4/1997 | Zysman et al. | |
| 5,665,778 A | 9/1997 | Semeria et al. | |
| 5,773,611 A | 6/1998 | Zysman et al. | |
| 5,869,711 A | 2/1999 | Philippe et al. | |
| 5,959,127 A | 9/1999 | Semeria et al. | |
| 6,001,376 A | 12/1999 | Mahieu et al. | |
| 6,039,936 A | 3/2000 | Restle et al. | |
| 6,039,939 A | 3/2000 | Ley et al. | |
| 6,039,963 A | 3/2000 | Philippe et al. | |
| 6,210,691 B1 | 4/2001 | Mahieu et al. | |
| 7,829,106 B2 * | 11/2010 | Hiyama ................... | A61K 8/86 424/400 |
| 8,394,755 B2 | 3/2013 | Andjelic et al. | |
| 2001/0023514 A1 | 9/2001 | Cottard et al. | |
| 2003/0185773 A1 | 10/2003 | Love et al. | |
| 2004/0180029 A1 | 9/2004 | Maubru | |
| 2005/0281763 A1 * | 12/2005 | Suginaka ................. | A61K 8/02 424/59 |
| 2006/0110415 A1 | 5/2006 | Gupta | |
| 2006/0140984 A1 * | 6/2006 | Tamarkin ........... | A61K 31/4174 424/400 |
| 2007/0098655 A1 | 5/2007 | Schmaus et al. | |
| 2007/0128146 A1 | 6/2007 | Fujino et al. | |
| 2008/0108709 A1 * | 5/2008 | Meyer ..................... | A61P 17/00 514/777 |
| 2010/0047296 A1 | 2/2010 | Banowski et al. | |
| 2010/0266510 A1 | 10/2010 | Tamarkin et al. | |

(Continued)

FOREIGN PATENT DOCUMENTS

| | | |
|---|---|---|
| CN | 1303666 A | 7/2001 |
| CN | 101267804 A | 9/2008 |

(Continued)

OTHER PUBLICATIONS

Machine English translation of Ding, CN 101530377, provided by Espacenet, accessed Mar. 23, 2020 (Year: 2009).*
Saxena et al. (Asian J. Biomed. Pharm. Sci., 2013, vol. 3, No. 22, pp. 16-22 (Year: 2013).*
Infinity Ingredients (<https://infinity-ingredients.co.uk/assets/uploads/market-sectors/Infinity-Certified-Natural-Ingredients-16.pdf.> Available Apr. 11, 2008) (21 pages) (Year: 2008).*

(Continued)

*Primary Examiner* — James D. Anderson
(74) *Attorney, Agent, or Firm* — The Marbury Law Group, PLLC

(57) ABSTRACT

The present invention relates to a composition, preferably a cosmetic composition, comprising: (a) at least one oil; (b) at least one polyglyceryl fatty acid ester, preferably with a polyglyceryl moiety derived from 2 to 6 glycerins; (c) at least one compound selected from the group consisting of resorcinol and resorcinol derivatives; and (d) water. The composition according to the present invention can be in the form of a nano- or micro-emulsion, or can have a lamellar structure or a lamellar phase, with better transparency and stability.

8 Claims, No Drawings

(56) References Cited

U.S. PATENT DOCUMENTS

| | | | | |
|---|---|---|---|---|
| 2011/0052512 A1* | 3/2011 | Monello | | A61K 8/06 424/59 |
| 2013/0039992 A1* | 2/2013 | Thompson | | A61K 9/0014 424/537 |
| 2015/0141508 A1 | 5/2015 | Klug et al. | | |

FOREIGN PATENT DOCUMENTS

| | | | |
|---|---|---|---|
| CN | 101401775 A | | 4/2009 |
| CN | 101530377 A | * | 9/2009 |
| CN | 101536962 A | | 9/2009 |
| CN | 101919791 A | | 12/2010 |
| CN | 102014661 A | | 4/2011 |
| CN | 102099001 A | | 6/2011 |
| CN | 102525843 A | | 7/2012 |
| CN | 102784084 A | | 11/2012 |
| CN | 104902864 A | | 9/2015 |
| DE | 4402929 C1 | | 6/1995 |
| DE | 4420736 C1 | | 8/1995 |
| DE | 4424530 A1 | | 1/1996 |
| DE | 4424533 A1 | | 1/1996 |
| EP | 0227994 A1 | | 7/1987 |
| EP | 0487958 A1 | | 6/1992 |
| EP | 0646572 A1 | | 4/1995 |
| EP | 0647617 A1 | | 4/1995 |
| EP | 0736522 A1 | | 10/1996 |
| FR | 2673179 A1 | | 8/1992 |
| JP | 09-110635 A | | 4/1997 |
| JP | 11-71256 A | | 3/1999 |
| JP | 2003-300855 A | | 10/2003 |
| JP | 2005-520849 A | | 7/2005 |
| JP | 2005-343864 A | | 12/2005 |
| JP | 2006-117643 A | | 5/2006 |
| JP | 2006-249011 A | | 9/2006 |
| JP | 2006-312622 A | | 11/2006 |
| JP | 2006-321769 A | | 11/2006 |
| JP | 2006-526005 A | | 11/2006 |
| JP | 2006-335693 A | | 12/2006 |
| JP | 2009-023947 A | | 2/2009 |
| JP | 2009-286735 A | | 12/2009 |
| JP | 2009-298748 A | | 12/2009 |
| JP | 2010-030910 A | | 2/2010 |
| JP | 2010-143858 A | | 7/2010 |
| JP | 2010-229068 A | | 10/2010 |
| JP | 2012-229193 A | | 11/2012 |
| JP | 2013-049633 A | | 3/2013 |
| JP | 2013-170154 A | | 9/2013 |
| JP | 2014-101294 A | | 6/2014 |
| JP | 2014-114256 A | | 6/2014 |
| WO | 94/07844 A1 | | 4/1994 |
| WO | 94/10131 A1 | | 5/1994 |
| WO | 94/24097 A1 | | 10/1994 |
| WO | 95/16665 A1 | | 6/1995 |
| WO | 95/23807 A1 | | 9/1995 |
| WO | 2009/075142 A | | 6/2009 |
| WO | 2012/079938 A1 | | 6/2012 |
| WO | 02/078650 A1 | | 10/2012 |
| WO | 2013/178683 A2 | | 12/2013 |
| WO | 2015/099198 A1 | | 7/2015 |

OTHER PUBLICATIONS

International Search Report and Written Opinion for PCT/JP2015/067379, dated Aug. 26, 2015.

Notification of Third Party Observation for counterpart JP Application No. 2014-130219, dated May 7, 2018 (with translation).

Japanese Office Action for counterpart JP Application No. 2014-130219, dated Jun. 4, 2018 (with translation).

Suzuki, "Basics on Emulsion Technologies Were Reviewed From the Following Viewpoints," J. Soc. Cosmet. Chem. Jpn., vol. 44, No. 2, pp. 103 and 104 (with English Abstract).

Non-Final Office Action for co-pending U.S. Appl. No. 15/129,961, dated Dec. 11, 2018.

Chinese Office Action for counterpart Application No. 201580031613.4, dated Jul. 12, 2019 with translation.

Partial translation of Chinese Office Action for counterpart Application No. 201580017621.3, dated Jan. 2, 2019 (Search Report Only).

Translated Chinese Office Action for counterpart Application No. 201580031613.4, dated Jun. 1, 2020.

International Search Report and Written Opinion for PCT/JP2015/060685, dated Jul. 10, 2015.

Davies, J.T., "A Quantitative Kinetic Theory of Emulsion Type. I. Physical Chemistry of the Emulsifying Agent," Reprinted from: Gas/Liquid and Liquid/Liquid Interfaces, Proceedings of 2nd International Congress Surface Activity, Butterworths, London, 1957, pp. 426-438.

L'Oreal, "Body Expertise Body Care Range," Mintel, XP-002740990, Database Accession No. 123056, Nov. 2001.

Perrin et al., "13 Emulsions Stabilized by Polyelectrolytes," Physical Chemistry of Polyelectrolytes, Surfactant Science Series, vol. 99, 2001, pp. 383-384.

Japanese Office Action for counterpart Application JP2014-075670, dated Apr. 16, 2018.

Notification received in connection with international application No. PCT/JP2015/060685; dated Jul. 30, 2016.

Office Action for co-pending U.S. Appl. No. 15/129,961, dated Sep. 5, 2017.

Final Office Action for co-pending U.S. Appl. No. 15/129,961, dated Mar. 30, 2018.

\* cited by examiner

COMPOSITION IN THE FORM OF NANO OR MICRO EMULSION OR WITH LAMELLAR STRUCTURE

CROSS REFERENCE TO RELATED APPLICATION

This is a national stage application of PCT/JP2015/067379, filed internationally on Jun. 10, 2015, which claims priority to Japanese Application No. 2014-130219, filed on Jun. 25, 2014, both of which are incorporated by reference herein in their entireties.

TECHNICAL FIELD

The present invention relates to a composition which is in the form of a nano- or micro-emulsion, or has a lamellar structure.

BACKGROUND ART

Oil-in-water (O/W) or Water-in-oil (W/O) emulsions are well known in the field of cosmetics and dermatology, in particular for the preparation of cosmetic products, such as milks, creams, tonics, serums or toilet waters.

It is known practice, in the cosmetics or dermatological field, to use oil-in-water (O/W) emulsions. These emulsions, that consist of an oil phase (or lipophilic phase) dispersed in an aqueous phase, have an external aqueous phase and are therefore products that are more pleasant to use because of the feeling of freshness that they provide.

In particular, a fine emulsion such as an O/W nano- or micro-emulsion is particularly interesting in cosmetic products due to its transparent or translucent aspect. For example, JP-A-2006-117643 discloses a micro emulsion which is formed by using a combination of specific nonionic surfactants.

On the other hand, compositions which have a lamellar structure or a lamellar phase are also well known in the field of cosmetics and dermatology. The term "lamellar structure" or "lamellar phase" means a liquid crystal structure or phase with plane symmetry, comprising several amphiphilic bilayers arranged in parallel and separated by a liquid medium which is generally water. For example JP-A-2006-249011 and JP-A-2009-298748 disclose cosmetic compositions with a lamellar structure with specific surfactants to form the amphiphilic bilayers.

Compositions with a lamellar structure or a lamellar phase can show optical effects, due to light interference by the lamellar structure or lamellar phase, such as rainbow color. Thus, the aesthetic aspect caused by the optical effects of the compositions with a lamellar structure or a lamellar phase can be in particular useful for cosmetic applications. In order to maximize the optical effects, transparency of the composition is required.

DISCLOSURE OF INVENTION

However, when a certain type of a nonionic surfactant is used for preparing a composition in the form of a fine emulsion such as a nano- or micro-emulsion, or a composition with a lamellar structure, the transparency of the composition, and the stability of the composition, are impaired.

An objective of the present invention is to provide a stable composition which can be in the form of a nano- or micro-emulsion, or can have a lamellar structure or a lamellar phase, with better transparency, even when the above nonionic surfactant is used.

The above objective of the present invention can be achieved by a composition, preferably a cosmetic composition, comprising:
(a) at least one oil;
(b) at least one polyglyceryl fatty acid ester, preferably with a polyglyceryl moiety derived from 2 to 6 glycerins;
(c) at least one compound selected from the group consisting of resorcinol and resorcinol derivatives; and
(d) water.

The composition can have a lamellar structure. In this case, the amount of the (a) oil may range from 0.01 to 20% by weight, preferably from 0.05 to 10% by weight, and more preferably from 0.1 to 5% by weight, relative to the total weight of the composition. The weight ratio of the (b) polyglyceryl fatty acid ester/the (a) oil may be from 1 to 30, preferably from 1 to 20, and more preferably from 1 to 10. The (b) polyglyceryl fatty acid ester may comprise a combination of two polyglyceryl fatty acid esters in which the HLB value of one polyglyceryl fatty acid ester is 10.0 or more, preferably 11.0 or more, and more preferably 12.0 or more, and the HLB value of the other polyglyceryl fatty acid ester is less than 10.0, preferably less than 9.8, and more preferably less than 9.6.

On the other hand, the composition can be in the form of a nano- or micro-emulsion. In this case, the amount of the (a) oil may range from 1 to 50% by weight, preferably from 5 to 40% by weight, and more preferably from 10 to 30% by weight, relative to the total weight of the composition. The weight ratio of the (b) polyglyceryl fatty acid ester/the (a) oil may be from 0.1 to 1, preferably from 0.3 to 1, and more preferably from 0.4 to 1. The (b) polyglyceryl fatty acid ester may have an HLB value of from 8.0 to 14.0, preferably from 9.0 to 13.5 and more preferably from 9.5 to 13.0. The composition according to the present invention may be in the form of an O/W emulsion wherein the (a) oil is in the form of a droplet with a number average particle size of 250 nm or less, preferably from 10 nm to 200 nm.

It is preferable that the (b) polyglyceryl fatty acid ester be chosen from polyglyceryl monolaurate comprising 3 to 6 glycerol units, polyglyceryl mono(iso)stearate comprising 3 to 6 glycerol units, polyglyceryl monooleate comprising 3 to 6 glycerol units, polyglyceryl dioleate comprising 3 to 6 glycerol units, and polyglyceryl monocaprate comprising 2 to 6 glycerol units.

The amount of the (b) polyglyceryl fatty acid ester may range from 0.1 to 25% by weight, preferably from 0.5 to 20% by weight, and more preferably from 1 to 15% by weight, relative to the total weight of the composition.

The resorcinol derivative may be a compound represented by the formula (I):

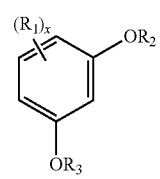

wherein
$R_1$ independently denotes -A-B where A represents a single bond, a $C_1$-$C_6$ alkylene group, a $C_{6-12}$ arylene group, or a $C_{1-6}$ alkylene-$C_{6-12}$ arylene group, and B represents a halogen atom, —OH, —COH, —COOH, —CONH$_2$, —NH$_2$, a $C_1$-$C_6$ alkyl group, a $C_{1-6}$ alkoxy group, a $C_{1-6}$ acyl group, a carbocyclic group, preferably an aryl group, or heterocyclic group, preferably a non-aromatic heterocyclic group, each of which may be substituted with at least one substituent selected from the group consisting of a hydroxyl group, a carboxyl group, a $C_{1-6}$ alkyl group, a $C_{1-6}$ alkylene-OH, an amino group, —CONH$_2$, —CONH—$C_{1-6}$ alkyl group and a $C_{1-6}$ alkoxy group; x is an integer of 1 to 4; and $R_2$ and $R_3$ independently denote a hydrogen atom, a $C_{1-6}$ alkyl group, or a $C_{1-6}$ acyl group, or a salt, a solvate, an optical isomer thereof, or a racemate thereof.

It is preferable that the resorcinol derivative be a compound represented by the formula (Ia):

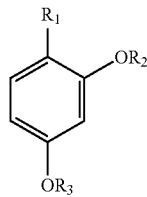

(Ia)

wherein $R_1$, $R_2$ and $R_3$ have the same meaning as above, or a salt, a solvate, an optical isomer thereof, or a racemate thereof.

It is more preferable that, in the above formula (Ia), $R^1$ denotes -A-B where A represents a single bond or a $C_{1-6}$ alkylene group, and B represents a phenyl group or a tetrahydropyranyl group; and each of $R_2$ and $R_3$ denote a hydrogen atom.

It is also preferable that the resorcinol derivative be a compound represented by the formula (II):

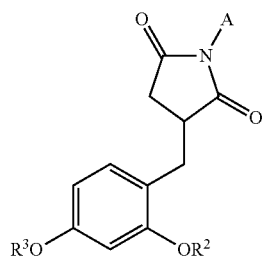

(II)

wherein $R_2$ and $R_3$ independently denote a hydrogen atom or an acetyl group;

A denotes a radical selected from:
a) —H;
b) a $C_3$-$C_8$ cyclic or $C_3$-$C_{20}$ branched or $C_2$-$C_{20}$ unsaturated or $C_1$-$C_{20}$ saturated linear alkyl group which is optionally interrupted by one or more heteroatoms or moieties selected from N, O and —CO— or a combination thereof such as —NHCO—, —NHCONH— and/or is optionally substituted by one or more identical or different groups selected from:
  i) —OR$_5$
  ii) —SR$_5$
  iii) —NR$_6$R$_7$
  iv) —CONHR$_6$
  v) —CONR$_6$R$_7$
  vi) —COOR$_6$
  vii) —NHCONHR$_6$
  viii) —C(O)C$_1$-C$_4$ alkyl
  ix) a $C_5$-$C_{12}$ (hetero)aryl group optionally containing one or more heteroatoms selected from O, N and S and optionally substituted by one or more hydroxyls and/or by one or more $C_1$-$C_8$ alkoxy radicals;
  x) a saturated or unsaturated, non-aromatic heterocycle having from 5 to 8 members and comprising one or more heteroatoms selected from O, N and S which is optionally substituted by one or more hydroxyls and/or by one or more $C_1$-$C_8$ alkoxy or $C_1$-$C_4$ alkyl radicals, it being possible for one of the members to be a carbonyl group;
c) a $C_5$-$C_{12}$ (hetero)aryl group optionally containing one or more heteroatoms selected from O, N and S and optionally substituted by one or more hydroxyls and/or by one or more radicals selected from $C_1$-$C_8$ alkoxy or $C_1$-$C_8$ alkyl groups;
d) —NR$_8$R$_9$;
e) —OR$_4$;
f) —C(O)NHR$_4$;
g) C(O)C$_1$-C$_{10}$ alkyl,
where $R_8$ and $R_9$, which are identical or different, denote a radical selected from:
a) —H;
b) a $C_3$-$C_8$ cyclic or $C_3$-$C_{10}$ branched or $C_2$-$C_{10}$ unsaturated or $C_1$-$C_{10}$ linear saturated alkyl group which is optionally interrupted by one or more heteroatoms or moieties selected from N, O and —CO— or a combination thereof such as —NHCO—, —NHCONH— and/or is optionally substituted by one or more identical or different groups selected from —OR$_5$;
c) a $C_5$-$C_{12}$ (hetero)aryl group optionally containing one or more heteroatoms selected from O, N and S and optionally substituted by one or more hydroxyls and/or by one or more $C_1$-$C_8$ alkoxy radicals;

it being possible for $R_8$ and $R_9$ to form, with the nitrogen which carries them, a heterocycle which has from 5 to 8 members and may contain one or more heteroatoms or moieties selected from N, O and —CO— and/or is optionally substituted by a $C_1$-$C_{10}$ hydrocarbon chain optionally containing one or more radicals selected from hydroxyl or $C_1$-$C_4$ alkoxy;

$R_4$ denotes a radical selected from:
a) —H
b) a $C_3$-$C_8$ cyclic or $C_3$-$C_{10}$ branched or $C_1$-$C_{10}$ linear saturated alkyl group which is optionally substituted by one or more identical or different groups selected from:
  i) —COOR$_6$,
  ii) a $C_5$-$C_{12}$ (hetero)aryl radical which optionally contains one or more heteroatoms selected from O, N and S and is optionally substituted by one or more hydroxyls and/or by one or more $C_1$-$C_8$ alkoxy radicals;
c) a $C_5$-$C_{12}$ (hetero)aryl group which optionally contains one or more heteroatoms selected from O, N and S and is optionally substituted by one or more hydroxyls and/or by one or more $C_1$-$C_8$ alkoxy radicals;

$R_5$ is selected from H and a $C_3$-$C_8$ cyclic or $C_2$-$C_{10}$ unsaturated or $C_3$-$C_{10}$ branched or $C_1$-$C_{10}$ linear saturated alkyl hydrocarbon group;

$R_6$ and $R_7$, which are identical or different, are selected from H, a $C_3$-$C_8$ cyclic or $C_2$-$C_{10}$ unsaturated or $C_3$-$C_{10}$ branched or $C_1$-$C_{10}$ linear saturated alkyl hydrocarbon group; a ($C_1$-$C_4$)alkyl-$C_6$ (hetero)aryl group optionally containing a nitrogen atom, more particularly a benzyl group;

$R_6$ and $R_7$ may form, with the nitrogen which carries them, a heterocycle which has from 5 to 8 members and may contain one or more heteroatoms or moieties selected from N, O and —CO— and/or is optionally substituted by a $C_1$-$C_{10}$ hydrocarbon chain;

h) a radical of formula (III):

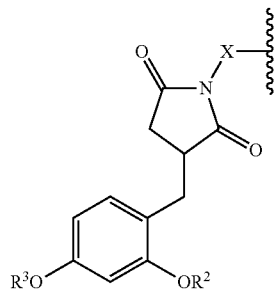

(III)

in which:

X denotes $C_3$-$C_8$ cyclic or $C_3$-$C_{10}$ branched or $C_1$-$C_{10}$ linear saturated hydrocarbon chain or a $C_6$-$C_{12}$ arylene group such as phenylene, or a $C_1$-$C_4$ alkylene-$C_6$-$C_8$ cycloalkylene-$C_1$-$C_4$ alkylene group or a $C_1$-$C_4$ alkylene-phenylene-$C_1$-$C_4$ alkylene group, which is optionally substituted by one or more identical or different radicals selected from —OH, —COOR$_6$ where $R_6$ denotes H or a $C_3$-$C_8$ cyclic or $C_2$-$C_{10}$ unsaturated or $C_3$-$C_{10}$ branched or $C_1$-$C_{20}$ linear saturated alkyl hydrocarbon group;

$R_2$ and $R_3$ have the same meaning as above; and when A denotes a radical of formula (III), all of the radicals $R_2$ and $R_3$ in the compounds of formula (II) are identical, or a salt, a solvate, an optical isomer thereof, or a racemate thereof.

It is preferable that $R_2$ and $R_3$ denote a hydrogen atom, and A denote a $C_3$-$C_{10}$ branched or $C_1$-$C_{10}$ linear saturated alkyl group.

The amount of the ingredient (c) (resorcinol and/or resorcinol derivative(s)) may range from 0.01 to 15% by weight, preferably from 0.1 to 10% by weight, and more preferably from 0.15 to 7% by weight, relative to the total weight of the composition.

Further, the present invention also relates to a cosmetic process for treating the skin, the hair, mucous membranes, the nails, the eyelashes, the eyebrows and/or the scalp, characterized in that the composition according to the present invention is applied to the skin, the hair, mucous membranes, the nails, the eyelashes, the eyebrows or the scalp.

Furthermore, the present invention also relates to a use of the composition according to the present invention, as it is or in care products and/or washing products and/or make-up products and/or make-up-removing products for body and/or facial skin and/or mucous membranes and/or the scalp and/or the hair and/or the nails and/or the eyelashes and/or the eyebrows.

BEST MODE FOR CARRYING OUT THE INVENTION

After diligent research, the inventors have discovered that it is possible to provide a stable composition which can be in the form of a nano- or micro-emulsion, or can have a lamellar structure or a lamellar phase, with better transparency, even when using a nonionic surfactant which was difficult to provide the composition with good transparency.

Thus, one aspect of the present invention is a composition, comprising:

(a) at least one oil;

(b) at least one polyglyceryl fatty acid ester, preferably with a polyglyceryl moiety derived from 2 to 6 glycerins;

(c) at least one compound selected from the group consisting of resorcinol and resorcinol derivatives; and (d) water.

The composition according to the present invention can have a dispersed phase which has a smaller diameter due to a combination of the ingredients (b) and (c). Therefore, the composition can be in the form of a transparent or translucent nano- or micro-emulsion with a better transparency.

Since the composition according to the present invention can have better transparency, the composition can be preferably used for cosmetics such as a lotion and a serum. Further, as the dispersed phase is finely dispersed, the composition according to the present invention can provide a unique texture, a moisturizing effect, and a moist feeling, as well as increased suppleness. Furthermore, if the dispersed phase is an oil phase and includes one or more lipophilic or even amphiphilic active ingredients, the dispersed oil phase can function as a carrier of the active ingredient and accelerate the penetration of the active ingredients into the skin, or can distribute the active ingredients on the skin.

On the other hand, the composition according to the present invention can have a lamellar structure or a lamellar phase due to a combination of the ingredients (b) and (c), with a better transparency. Therefore, the composition can provide unique optical effects such as a rainbow-like appearance.

As mentioned above, since the composition according to the present invention can have better transparency, the composition can be preferably used for cosmetics such as a lotion and a serum. Further, as a lamellar structure or a lamellar phase can increase the viscosity of the composition according to the present invention, it can be used without dripping. On the other hand, once the composition according to the present invention having a lamellar structure or a lamellar phase is applied onto the skin, for example, the lamellar structure or phase can easily break, and therefore, the viscosity of the composition can be reduced, and the composition can easily spread over the skin while providing a good feeling to use. Furthermore, the lamellar structure can include water, and therefore, it can improve the feeling to use, while it can be compatible with a hydrophobic substance such as sebum. In addition, the composition according to the present invention having a lamellar structure or a lamellar phase can easily form an emulsion when a relatively large amount of water is added. Accordingly, the composition according to the present invention having a lamellar structure or a lamellar phase can be easily washed off with water.

Hereinafter, the composition according to the present invention will be explained in a more detailed manner.

The composition according to the present invention comprises (a) at least one oil. Here, "oil" means a fatty compound or substance which is in the form of a liquid or a paste (non-solid) at room temperature (25° C.) under atmospheric pressure (760 mmHg). As the oil(s), those generally used in cosmetics can be used alone or in combination thereof. These oil(s) may be volatile or non-volatile, preferably non-volatile.

The (a) oil may be a non-polar oil such as a hydrocarbon oil, a silicone oil, or the like; a polar oil such as a plant or animal oil and an ester oil or an ether oil; or a mixture thereof.

It is preferable that the (a) oil be selected from the group consisting of oils of plant or animal origin, synthetic oils, silicone oils and hydrocarbon oils.

As examples of plant oils, mention may be made of, for example, linseed oil, camellia oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, and mixtures thereof.

As examples of animal oils, mention may be made of, for example, squalene and squalane.

As examples of synthetic oils, mention may be made of alkane oils such as isododecane and isohexadecane, ester oils, ether oils, and artificial triglycerides.

The ester oils are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the invention are derived is branched.

Among the monoesters of monoacids and of monoalcohols, mention may be made of ethyl palmitate, ethyl hexyl palmitate, isopropyl palmitate, dicaprylyl carbonate, alkyl myristates such as isopropyl myristate or ethyl myristate, isocetyl stearate, 2-ethylhexyl isononanoate, isononyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of non-sugar $C_4$-$C_{26}$ dihydroxy, trihydroxy, tetrahydroxy or pentahydroxy alcohols may also be used.

Mention may especially be made of: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

As ester oils, one can use sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters, as well as pentaerythrityl tetraethyl hexanoate.

More particularly, use is made of monoesters and diesters and especially sucrose, glucose or methylglucose monooleates or dioleates, stearates, behenates, oleopalmitates, linoleates, linolenates and oleostearates.

An example that may be mentioned is the product sold under the name Glucate® DO by the company Amerchol, which is a methylglucose dioleate.

As examples of preferable ester oils, mention may be made of, for example, diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethylhexanoate), 2-ethylhexyl succinate, diethyl sebacate, and mixtures thereof.

As examples of artificial triglycerides, mention may be made of, for example, capryl caprylyl glycerides, glyceryl trimyristate, glyceryl tripalmitate, glyceryl trilinolenate, glyceryl trilaurate, glyceryl tricaprate, glyceryl tricaprylate, glyceryl tri(caprate/caprylate) and glyceryl tri(caprate/caprylate/linolenate).

As examples of silicone oils, mention may be made of, for example, linear organopolysiloxanes such as dimethylpolysiloxane, methylphenylpolysiloxane, methylhydrogenpolysiloxane, and the like; cyclic organopolysiloxanes such as octamethylcyclotetrasiloxane, decamethylcyclopentasiloxane, dodecamethylcyclohexasiloxane, and the like; and mixtures thereof.

Preferably, silicone oil is chosen from liquid polydialkylsiloxanes, especially liquid polydimethylsiloxanes (PDMS) and liquid polyorganosiloxanes comprising at least one aryl group.

These silicone oils may also be organomodified. The organomodified silicones that can be used in accordance with the present invention are silicone oils as defined above and comprising in their structure one or more organofunctional groups attached via a hydrocarbon-based group.

Organopolysiloxanes are defined in greater detail in Walter Noll's *Chemistry and Technology of Silicones* (1968), Academic Press. They may be volatile or non-volatile.

When they are volatile, the silicones are more particularly chosen from those having a boiling point of between 60° C. and 260° C., and even more particularly from:

(i) cyclic polydialkylsiloxanes comprising from 3 to 7 and preferably 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, Silbione® 70045 V5 by Rhodia, and dodecamethylcyclopentasiloxane sold under the name Silsoft® 1217 by Momentive Performance Materials, and mixtures thereof. Mention may also be made of cyclocopolymers of the type such as dimethylsiloxane/methylalkylsiloxane, such as Silicone Volatile® FZ 3109 sold by the company Union Carbide, of formula:
with D":

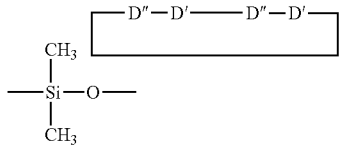

with D':

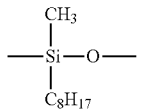

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2', 2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics*. The viscosity of the silicones is measured at 25° C. according to ASTM standard 445 Appendix C.

Non-volatile polydialkylsiloxanes may also be used. These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:
  the Silbione® oils of the 47 and 70 047 series or the Mirasil® oils sold by Rhodia, for instance the oil 70 047 V 500 000;
  the oils of the Mirasil® series sold by the company Rhodia;
  the oils of the 200 series from the company Dow Corning, such as DC200 with a viscosity of 60 000 mm$^2$/s;
  the Viscasil® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from the company Rhodia.

Among the silicones containing aryl groups are polydiarylsiloxanes, especially polydiphenylsiloxanes and polyalkylarylsiloxanes. Examples that may be mentioned include the products sold under the following names:
  the Silbione® oils of the 70 641 series from Rhodia;
  the oils of the Rhodorsil® 70 633 and 763 series from Rhodia;
  the oil Dow Corning 556 Cosmetic Grade Fluid from Dow Corning;
  the silicones of the PK series from Bayer, such as the product PK20;
  certain oils of the SF series from General Electric, such as SF 1023, SF 1154, SF 1250 and SF 1265.

The organomodified liquid silicones may especially contain polyethyleneoxy and/or polypropyleneoxy groups. Mention may thus be made of the silicone KF-6017 proposed by Shin-Etsu, and the oils Silwet® L722 and L77 from the company Union Carbide.

Hydrocarbon oils may be chosen from:
  linear or branched, optionally cyclic, $C_6$-$C_{16}$ lower alkanes. Examples that may be mentioned include hexane, undecane, dodecane, tridecane, and isoparaffins, for instance isohexadecane, isododecane and isodecane; and
  linear or branched hydrocarbons containing more than 16 carbon atoms, such as liquid paraffins, liquid petroleum jelly, polydecenes and hydrogenated polyisobutenes such as Parleam®, and squalane.

As preferable examples of hydrocarbon oils, mention may be made of, for example, linear or branched hydrocarbons such as isohexadecane, isododecane, squalane, mineral oil (e.g., liquid paraffin), paraffin, vaseline or petrolatum, naphthalenes, and the like; hydrogenated polyisobutene, isoeicosane, and decene/butene copolymer; and mixtures thereof.

It is preferable that the (a) oil be chosen from hydrocarbon oils which are in the form of a liquid at a room temperature.

It is also preferable that the (a) oil be chosen from oils with molecular weight below 600 g/mol.

Preferably, the (a) oil has a low molecular weight such as below 600 g/mol, chosen among ester or ether oils with a short hydrocarbon chain or chains ($C_1$-$C_{12}$, e.g., isopropyl myristate, isopropyl palmitate, isononyl isononanoate, dicaprylyl carbonate, ethyl hexyl palmitate, dicaprylyl ether, and isopropyl lauroyl sarcosinate), hydrocarbon oils with a short alkyl chain or chains ($C_1$-$C_{12}$, e.g., isododecane, isohexadecane, and squalane), and short alcohol type oils such as octyldodecanol.

It is also preferable that the (a) oil be selected from the group consisting of hydrocarbon oils, esters of $C_4$-$C_{22}$ dicarboxylic or tricarboxylic acids and of $C_1$-$C_{22}$ alcohols, and esters of $C_4$-$C_{22}$ monocarboxylic, dicarboxylic or tricarboxylic acids and of non-sugar $C_4$-$C_{26}$ dihydroxy, $C_4$-$C_{15}$ trihydroxy, tetrahydroxy or pentahydroxy alcohols.

The amount in the composition according to the present invention of the (a) oil is not limited, and may range from 0.1 to 50% by weight, preferably from 0.5 to 40% by weight, and more preferably from 1 to 30% by weight, relative to the total weight of the composition, if the composition according to the present invention is in the form of a nano- or micro-emulsion.

On the other hand, if the composition according to the present invention has a lamellar structure or a lamellar phase, the amount of the (a) oil may range from 0.01 to 20% by weight, preferably from 0.05 to 10% by weight, and more preferably from 0.1 to 5% by weight, relative to the total weight of the composition.

[Polyglyceryl Fatty Acid Ester]

The composition according to the present invention comprises (b) at least one polyglyceryl fatty acid ester. A single type of polyglyceryl fatty acid ester may be used, but two or more different types of polyglyceryl fatty acid ester may be used in combination.

In order to form a nano- or micro-emulsion, it is preferable that the (b) polyglyceryl fatty acid ester have a polyglycerol moiety derived from 2 to 10 glycerols, more preferably from 3 to 6 glycerols, and further more preferably 5 or 6 glycerols.

In order to form a nano- or micro-emulsion, it is preferable that the (b) polyglyceryl fatty acid ester have an HLB (Hydrophilic Lipophilic Balance) value of from 8.0 to 14.0, preferably from 9.0 to 13.5, and more preferably from 9.5 to 13.0.

In order to form a lamellar structure or a lamellar phase, it is preferable to use a combination of two or more (b) polyglyceryl fatty acid esters with different polyglycerol moieties. It is more preferable to use a combination of polyglyceryl fatty acid ester having a polyglycerol moiety derived from 2 to 3 glycerols, more preferably 2 glycerols and polyglyceryl fatty acid ester having a polyglycerol moiety derived from 4 to 6 glycerols, more preferably 5 glycerols.

In order to form a lamellar structure or a lamellar phase, it is preferable to use a combination of two or more (b) polyglyceryl fatty acid esters with different HLB values. It is more preferable to use a combination of two polyglyceryl fatty acid esters in which the HLB value of one polyglyceryl fatty acid ester is 10.0 or more, preferably 11.0 or more, and more preferably 12.0 or more, and the HLB value of the other polyglyceryl fatty acid ester is less than 10.0, preferably less than 9.8, and more preferably less than 9.6.

The (b) polyglyceryl fatty acid ester may be chosen from the mono, di and tri esters of saturated or unsaturated fatty acid, including 2 to 30 carbon atoms, preferably 6 to 30 carbon atoms, and more preferably 8 to 30 carbon atoms, such as lauric acid, oleic acid, stearic acid, isostearic acid, capric acid, caprylic acid, and myristic acid.

The polyglyceryl fatty acid ester may be selected from the group consisting of PG2 caprate, PG2 dicaprate, PG2 tricaprate, PG2 caprylate, PG2 dicaprylate, PG2 tricaprylate, PG2 laurate, PG2 dilaurate, PG2 trilaurate, PG2 myristate, PG2 dimyristate, PG2 trimyristate, PG2 stearate, PG2 distearate, PG2 tristearate, PG2 isostearate, PG2 diisostearate, PG2 triisostearate, PG2 oleate, PG2 dioleate, PG2 trioleate, PG3 caprate, PG3 dicaprate, PG3 tricaprate, PG3 caprylate, PG3 dicaprylate, PG3 tricaprylate, PG3 laurate, PG3 dilaurate, PG3 trilaurate, PG3 myristate, PG3 dimyristate, PG3 trimyristate, PG3 stearate, PG3 distearate, PG3 tristearate, PG3 isostearate, PG3 diisostearate, PG3 triisostearate, PG3 oleate, PG3 dioleate, PG3 trioleate, PG4 caprate, PG4 dicaprate, PG4 tricaprate, PG4 caprylate, PG4 dicaprylate, PG4 tricaprylate, PG4 laurate, PG4 dilaurate, PG4 trilaurate, PG4 myristate, PG4 dimyristate, PG4 trimyristate, PG4 stearate, PG4 distearate, PG4 tristearate, PG4 isostearate, PG4 diisostearate, PG4 triisostearate, PG4 oleate, PG4 dioleate, PG4 trioleate, PG5 caprate, PG5 dicaprate, PG5 tricaprate, PG5 caprylate, PG5 dicaprylate, PG5 tricaprylate, PG5 laurate, PG5 dilaurate, PG5 trilaurate, PG5 myristate, PG5 dimyristate, PG5 trimyristate, PG5 stearate, PG5 distearate, PG5 tristearate, PG5 isostearate, PG5 diisostearate, PG5 triisostearate, PG5 oleate, PG5 dioleate, PG5 trioleate, PG6 caprate, PG6 dicaprate, PG6 tricaprate, PG6 caprylate, PG6 dicaprylate, PG6 tricaprylate, PG6 laurate, PG6 dilaurate, PG6 trilaurate, PG6 myristate, PG6 dimyristate, PG6 trimyristate, PG6 stearate, PG6 distearate, PG6 tristearate, PG6 isostearate, PG6 diisostearate, PG6 triisostearate, PG6 oleate, PG6 dioleate, PG6 trioleate, PG10 caprate, PG10 dicaprate, PG10 tricaprate, PG10 caprylate, PG10 dicaprylate, PG10 tricaprylate, PG10 laurate, PG10 dilaurate, PG10 trilaurate, PG10 myristate, PG10 dimyristate, PG10 trimyristate, PG10 stearate, PG10 distearate, PG10 tristearate, PG10 isostearate, PG10 diisostearate, PG10 triisostearate, PG10 oleate, PG10 dioleate, and PG10 trioleate.

It is preferable that the (b) polyglyceryl fatty acid ester be chosen from:
polyglyceryl monolaurate comprising 3 to 6 glycerol units,
polyglyceryl mono(iso)stearate comprising 3 to 6 glycerol units,
polyglyceryl monooleate comprising 3 to 6 glycerol units,
polyglyceryl dioleate comprising 3 to 6 glycerol units, and
polyglyceryl monocaprate comprising 2 to 6 glycerol units.

In one embodiment, the (b) polyglyceryl fatty acid ester raw material may be chosen from a mixture of polyglyceryl fatty acid esters, preferably with a polyglyceryl moiety derived from 2 to 6 glycerins, more preferably 5 or 6 glycerins, wherein the mixture preferably comprises 30% by weight or more of a polyglyceryl fatty acid ester with a polyglyceryl moiety consisting of 5 or 6 glycerins.

It is preferable that the (b) polyglyceryl fatty acid ester raw material comprise esters of a fatty acid and polyglycerine containing 70% or more of polyglycerine whose polymerization degree is 4 or more, preferably esters of a fatty acid and polyglycerine containing equal to or more than 60% of polyglycerine whose polymerization degree is between 4 and 11, and more preferably esters of a fatty acid and polyglycerine containing equal to or more than 30% of polyglycerine whose polymerization degree is 5.

The amount in the composition according to the present invention of the (b) polyglyceryl fatty acid ester is not limited, and may range from 0.1 to 25% by weight, preferably from 0.5 to 20% by weight, and more preferably from 1 to 15% by weight, relative to the total weight of the composition.

In the case in which the composition according to the present invention is in the form of a nano- or micro-emulsion, it may be preferable that the amount in the composition according to the present invention of the (b) polyglyceryl fatty acid ester range from 1 to 25% by weight, preferably from 3 to 20% by weight, and more preferably from 5 to 15% by weight, relative to the total weight of the composition.

In the case in which the composition according to the present invention has a lamellar structure or a lamellar phase, it may be preferable that the amount in the composition according to the present invention of the (b) polyglyceryl fatty acid ester range from 0.1 to 25% by weight, preferably from 0.5 to 20% by weight, and more preferably from 1 to 15% by weight, relative to the total weight of the composition.

In the case in which the composition according to the present invention is in the form of a nano- or micro-emulsion, it is preferable that the weight ratio of the (b) polyglyceryl fatty acid ester/(a) oil be from 0.1 to 1, more preferably from 0.3 to 1, and even more preferably from 0.4 to 1.

In the case in which the composition according to the present invention has a lamellar structure or a lamellar phase, it is preferable that the weight ratio of the (b) polyglyceryl fatty acid ester/(a) oil be from 1 to 30, more preferably from 1 to 20, and even more preferably from 1 to 10.

[Resorcinol or Resorcinol Derivative]

The composition according to the present invention comprises (c) at least one compound selected from the group consisting of resorcinol and resorcinol derivatives. A combination of resorcinol and a resorcinol derivative may be used. A single type of resorcinol derivative may also be used, but two or more different types of resorcinol derivative may be used in combination.

In one embodiment, the resorcinol derivative may be a compound represented by the formula (I):

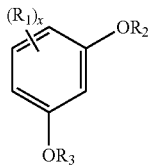

(I)

wherein $R_1$ independently denotes -A-B where A represents a single bond, a $C_1$-$C_6$ alkylene group, a $C_{6-12}$ arylene group, or a $C_{1-6}$ alkylene-$C_{602}$ arylene group, and B represents a halogen atom, —OH, —COH, —COOH, —CONH$_2$, —NH$_2$, a $C_1$-$C_6$ alkyl group, a $C_{1-6}$ alkoxy group, a $C_{1-6}$ acyl group, a carbocyclic group, preferably an aryl group, or heterocyclic group, preferably a non-aromatic heterocyclic group, each of which may be substituted with at least one substituent selected from the group consisting of a hydroxyl group, a carboxyl group, a $C_{1-6}$ alkyl group, a $C_{1-6}$ alkylene-OH, an amino group, —CONH$_2$, —CONH—$C_{1-6}$ alkyl group and a $C_{1-6}$ alkoxy group;

x is an integer of 1 to 4, preferably 1 to 3, more preferably 1 or 2 and even more preferably 1; and $R_2$ and $R_3$ independently denote a hydrogen atom, a $C_{1-6}$ alkyl group, or a $C_{1-6}$ acyl group, or a salt, a solvate, an optical isomer thereof, or a racemate thereof.

The $C_1$-$C_6$ alkylene group may be a straight or branched divalent group.

The $C_{1-6}$ alkylene-$C_{6-12}$ arylene group may also be a straight or branched divalent group. Either the $C_{1-6}$ alkylene moiety or the $C_{6-12}$ arylene moiety may bond the dihydroxy benzene ring shown in the formula (I).

The aryl group as "B" may be a $C_{6-12}$ aryl group such as a phenyl group, a tolyl group and a xylyl group, or a naphtyl group.

The hetero atom in the heterocyclic group as "B" may be an oxygen atom, a sulfur atom and a nitrogen atom. A single heteroatom or a plurality of hetero atoms may be included in the heterocyclic group. As examples of the heterocyclic group, mention may be made of a furanyl group, a pyrrole group, an oxazole group, an isoxazolyl group, a thiazolyl group, an isothiazolyl group, an imidazolyl group, a pyrazolyl group, a pyranyl group, a pyridinyl group, a pyridazinyl group, a pyrimidinyl group, a pyrazinyl group, an indolyl group, an isoindolyl group, a benzofuranyl group, a quinolinyl group, isoquinolinyl group and an indazolyl group.

As examples of the non-aromatic heterocyclic group, mention may be made of a pyrrolidinyl group, an imidazolidinyl group, a pyrazolidinyl group, a piperidinyl group, a piperazinyl group, a morpholinyl group, and a tetrahydropyranyl group.

As examples of the compound according to formula (I), mention may be made of 2-methylresorcinol, 5-methylresorcinol, 4-methylresorcinol, 2,4-dihydroxybenzaldehyde, 4-ethylresorcinol, 2,5-dimethylresorcinol, 4,5-dimethylresorcinol, 2,4-dimethyl-1,3-benzenediol, 3,5-dihydroxybenzylamine, 5-methoxyresorcinol, 3,5-dihydroxybenzyl alcohol, 2-methoxyresorcinol, 4-methoxyresorcinol, 3,5-dihydroxytoluene monohydrate, 4-chlororesorcinol, 2-chlororesorcinol, 2',4'-dihydroxyacetophenone, 3',5'-dihydroxyacetophenone, 2,6-dihydroxy-4-methylbenzaldehyde, 4-propylresorcinol, 2,4-dihydroxy-1,3,5-trimethylbenzene, 3,5-dihydroxybenzamide, 2,6-dihydroxybenzamide, 2,4-dihydroxybenzamide, 2,4-dihydroxybenzoic acid, 2,6-dihydroxybenzoic acid, 3,5-dihydroxybenzoic acid, 2,6-dihydroxy-4-methylbenzyl alcohol, 3,5-dihydroxyanisole hydrate, 4-aminoresorcinol hydrochloride, 2-aminoresorcinol hydrochloride, 5-aminobenzene-1,3-diol hydrochloride, 2',4'-dihydroxypropiophenone, 2',4'-dihydroxy-3'-methylacetophenone, (2,4-dihydroxyphenyl)acetone, (3,5-dihydroxyphenyl)acetone, 2,6-dihydroxy-4'-methylacetophenone, 4-n-butylresorcinol, 2,4-diethyl-1,3-benzenediol, 3,5-dihydroxy-4-methylbenzoic acid, 2,6-dihydroxy-4-methylbenzoic acid, 2,4-dihydroxy-6-methylbenzoic acid, 3,5-dihydroxyphenylacetic acid, 2-ethyl-5-methoxybenzene-1,3-diol, 4-amino-3,5-dihydroxybenzoic acid, 3,5-dihydroxyacetophenone monohydrate, 3,5-dihydroxybenzylamine hydrochloride, 4,6-dichlororesorcinol, 2',4'-dihydroxy-3'-methylpropiophenone, 1-(3-ethyl-2,6-dihydroxyphenyl)ethan-1-one, 2',6'-dihydroxy-4'-methoxyacetophenone, 1-(2,6-dihydroxy-3-methoxyphenyl)ethan-1-one, 3(2,4-dihydroxyphenylpropionic acid, and 2,4-dihydroxy-3,6-dimethylbenzoic acid.

It is preferable that the resorcinol derivative be a compound represented by the formula (Ia):

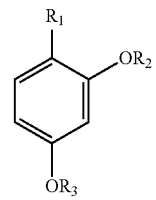

(Ia)

wherein $R_1$, $R_2$ and $R_3$ have the same meaning as above, or a salt, a solvate, an optical isomer thereof, or a racemate thereof.

It is more preferable that, in the above formula (Ia), $R^1$ denote -A-B where A represents a single bond or a $C_{1-6}$ alkylene group, and B represents a phenyl group or a tetrahydropyranyl group; and each of $R_2$ and $R_3$ denote a hydrogen atom.

It is even more preferable that the resorcinol derivative be phenylethyl resorcinol and 4-(tetrahydro-2H-pyran-4-yl)benzene-1,3-diol.

It is also preferable that the resorcinol derivative be a compound represented by the formula (II):

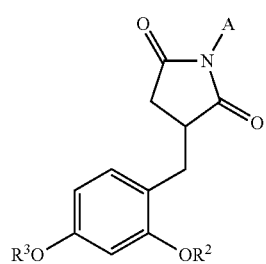

(II)

wherein $R_2$ and $R_3$ independently denote a hydrogen atom or an acetyl group;

A denotes a radical selected from:
a) —H;
b) a $C_3$-$C_8$ cyclic or $C_3$-$C_{20}$ branched or $C_2$-$C_{20}$ unsaturated or $C_1$-$C_{20}$ saturated linear alkyl group which is optionally interrupted by one or more heteroatoms or moieties selected from N, O and —CO— or a combination thereof such as —NHCO—, —NHCONH— and/or is optionally substituted by one or more identical or different groups selected from:
  i) —$OR_5$
  ii) —$SR_5$
  iii) —$NR_6R_7$
  iv) —$CONHR_6$
  v) —$CONR_6R_7$
  vi) —$COOR_6$
  vii) —$NHCONHR_6$
  viii) —$C(O)C_1$-$C_4$ alkyl
  ix) a $C_5$-$C_{12}$ (hetero)aryl group optionally containing one or more heteroatoms selected from O, N and S and optionally substituted by one or more hydroxyls and/or by one or more $C_1$-$C_8$ alkoxy radicals;
  x) a saturated or unsaturated, non-aromatic heterocycle having from 5 to 8 members and comprising one or more heteroatoms selected from O, N and S which is optionally substituted by one or more hydroxyls and/or by one or more $C_1$-$C_5$ alkoxy or $C_1$-$C_4$ alkyl radicals, it being possible for one of the members to be a carbonyl group;

c) a $C_5$-$C_{12}$ (hetero)aryl group optionally containing one or more heteroatoms selected from O, N and S and optionally substituted by one or more hydroxyls and/or by one or more radicals selected from $C_1$-$C_8$ alkoxy or $C_1$-$C_8$ alkyl groups;

d) —$NR_8R_9$;
e) —$OR_4$;
f) —$C(O)NHR_4$;
g) $C(O)C_1$-$C_{10}$ alkyl, where $R_8$ and $R_9$, which are identical or different, denote a radical selected from:
a) —H;
b) a $C_3$-$C_8$ cyclic or $C_3$-$C_{10}$ branched or $C_2$-$C_{10}$ unsaturated or $C_1$-$C_{10}$ linear saturated alkyl group which is optionally interrupted by one or more heteroatoms or moieties selected from N, O and —CO— or a combination thereof such as —NHCO—, —NHCONH— and/or is optionally substituted by one or more identical or different groups selected from —$OR_5$;
c) a $C_5$-$C_{12}$ (hetero)aryl group optionally containing one or more heteroatoms selected from O, N and S and optionally substituted by one or more hydroxyls and/or by one or more $C_1$-$C_8$ alkoxy radicals;

it being possible for $R_8$ and $R_9$ to form, with the nitrogen which carries them, a heterocycle which has from 5 to 8 members and may contain one or more heteroatoms or moieties selected from N, O and —CO— and/or is optionally substituted by a $C_1$-$C_{10}$ hydrocarbon chain optionally containing one or more radicals selected from hydroxyl or $C_1$-$C_4$ alkoxy;

$R_4$ denotes a radical selected from:
a) —H
b) a $C_3$-$C_8$ cyclic or $C_3$-$C_{10}$ branched or $C_1$-$C_{10}$ linear saturated alkyl group which is optionally substituted by one or more identical or different groups selected from:
  i) —$COOR_6$,
  ii) a $C_5$-$C_{12}$ (hetero)aryl radical which optionally contains one or more heteroatoms selected from O, N and S and is optionally substituted by one or more hydroxyls and/or by one or more $C_1$-$C_8$ alkoxy radicals;
c) a $C_5$-$C_{12}$ (hetero)aryl group which optionally contains one or more heteroatoms selected from O, N and S and is optionally substituted by one or more hydroxyls and/or by one or more $C_1$-$C_8$ alkoxy radicals;

$R_5$ is selected from H and a $C_3$-$C_8$ cyclic or $C_2$-$C_{10}$ unsaturated or $C_3$-$C_{10}$ branched or $C_1$-$C_{10}$ linear saturated alkyl hydrocarbon group;

$R_6$ and $R_7$, which are identical or different, are selected from H, a $C_3$-$C_8$ cyclic or $C_2$-$C_{10}$ unsaturated or $C_3$-$C_{10}$ branched or $C_1$-$C_{10}$ linear saturated alkyl hydrocarbon group; a $(C_1$-$C_4)$alkyl-$C_6$ (hetero)aryl group optionally containing a nitrogen atom, more particularly a benzyl group;

$R_6$ and $R_7$ may form, with the nitrogen which carries them, a heterocycle which has from 5 to 8 members and may contain one or more heteroatoms or moieties selected from N, O and —CO— and/or is optionally substituted by a $C_1$-$C_{10}$ hydrocarbon chain;

h) a radical of formula (III):

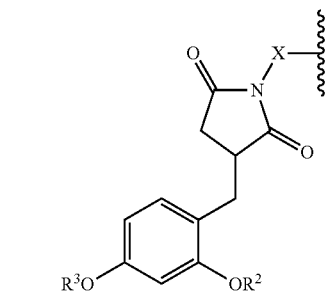

(III)

in which:

X denotes a $C_3$-$C_8$ cyclic or $C_3$-$C_{10}$ branched or $C_1$-$C_{10}$ linear saturated hydrocarbon chain or a $C_6$-$C_{12}$ arylene group such as phenylene, or a $C_1$-$C_4$ alkylene-$C_6$-$C_8$ cycloalkylene-$C_1$-$C_4$ alkylene group or a $C_1$-$C_4$ alkylene-phenylene-$C_1$-$C_4$ alkylene group, which is optionally substituted by one or more identical or different radicals selected from —OH, —$COOR_6$ where $R_6$ denotes H or a $C_3$-$C_8$ cyclic or $C_2$-$C_{10}$ unsaturated or $C_3$-$C_{10}$ branched or $C_1$-$C_{20}$ linear saturated alkyl hydrocarbon group;

$R_2$ and $R_3$ have the same meaning as above; and when A denotes a radical of formula (III), all of the radicals $R_2$ and $R_3$ in the compounds of formula (II) are identical, or a salt, a solvate, an optical isomer thereof, or a racemate thereof.

The salts of the compounds of formulae (I) and (II) include conventional non-toxic salts of said compounds, such as those formed from an acid or from a base.

Salts of the compound of formulae (I) and (II) (when it comprises a quaternizable nitrogen atom) include the following:

a) salts obtained by addition of the compound (I) or (II) with a mineral acid, selected more particularly from hydrochloric, boric, hydrobromic, hydroic, sulphuric, nitric, carbonic, phosphoric and tetrafluoroboric acids;

b) or the salts obtained by addition of the compound (I) or (II) with an organic acid, more particularly selected from acetic, propionic, succinic, fumaric, lactic, glycolic, citric, gluconic, salicylic, tartaric, terephthalic, methylsulphonic, ethylsulphonic, benzene sulphonic, toluene sulphonic and triflic acids.

Also included are the salts obtained by addition of the compound of formula (I) or (II) (when it comprises an acidic group) with a mineral base, such as aqueous sodium hydroxide and potassium hydroxide, calcium hydroxide, ammonium hydroxide, magnesium hydroxide, lithium hydroxide, and sodium, potassium or calcium carbonates or hydrogencarbonates, for example; or with an organic base such as a primary, secondary or tertiary alkylamine, for example triethylamine or butylamine. This primary, secondary or tertiary alkylamine may comprise one or more nitrogen and/or oxygen atoms and may therefore comprise, for example, one or more alcohol functions; included more particularly are 2-amino-2-methylpropanol, ethanolamine, triethanolamine, 2-dimethylamino propanol, 2-amino-2-(hydroxymethyl)-1, 3-propanediol and 3-(dimethylamino)propylamine.

Also included are the salts of amino acids such as, for example, lysine, arginine, guanidine, glutamic acid and aspartic acid.

The salts of the compounds of formulae (I) and (II) (when it comprises an acidic group) may advantageously be selected from alkali metal salts or alkaline earth metal salts such as sodium, potassium, calcium and magnesium salts; and ammonium salts.

The salts of the compounds of formulae (I) and (II) (when it comprises a quaternizable nitrogen atom) may advantageously be selected from halides such as chloride and bromide; and from citrates, acetates, succinates, phosphates, lactates and tartrates.

The acceptable solvates of the compounds described in the present invention comprise conventional solvates such as those formed during the preparation of said compounds as a result of the presence of solvents. Examples include the solvates resulting from the presence of water or of linear or branched alcohols such as ethanol or isopropanol.

The optical isomers are more particularly enantiomers and diastereoisomers.

The linear or branched groups may preferably be selected from methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl.

The saturated linear or branched alkyl groups may more preferably be selected from methyl, ethyl, propyl, isopropyl, butyl, isobutyl, tert-butyl, pentyl, hexyl, heptyl and octyl.

The $C_1$-$C_4$ alkoxy groups may preferably be selected from methoxy, ethoxy, propoxy and butoxy and more preferably methoxy.

The compounds of formula (II) preferably have the following meanings:

$R_2$ and $R_3$ independently denote a hydrogen atom or an acetyl group;

A denotes a radical selected from:
a) —H
b) a $C_3$-$C_8$ cyclic or $C_3$-$C_{16}$ branched or $C_2$-$C_{16}$ unsaturated or $C_1$-$C_{16}$ linear saturated alkyl group which is optionally interrupted by one or more heteroatoms or moieties selected from N, O, —CO— and —NHC(O)— and/or is optionally substituted by one or more identical or different groups selected from:
  i) —OH,
  ii) $C_1$-$C_4$ alkoxy,
  iii) —COOR$_6$,
  iv) —CONR$_6$R$_7$ where $R_6$ and $R_7$, which are identical or different, denote H or a $C_3$-$C_8$ cyclic or $C_2$-$C_8$ unsaturated or $C_3$-$C_8$ branched or $C_1$-$C_8$ linear saturated alkyl group;
  v) a phenyl group which is optionally substituted by one or more hydroxyls and/or by one or more $C_1$-$C_4$ alkoxy radicals;
  vi) a non-aromatic saturated or unsaturated heterocycle having from 5 to 8 members, comprising one or more heteroatoms selected from O, N and S, it being possible for one of the members to be a carbonyl group;
c) a $C_5$-$C_{12}$ aryl group such as phenyl which is optionally substituted by one or more identical or different radicals selected from OH, $C_1$-$C_4$ alkoxy and $C_1$-$C_4$ alkyl;
d) —NR$_8$R$_9$, where $R_8$ and $R_9$, which are identical or different, denote:
  i) H;
  ii) a $C_3$-$C_8$ cyclic or $C_2$-$C_8$ unsaturated or $C_3$-$C_8$ branched or $C_1$-$C_8$ linear saturated alkyl group which is optionally interrupted by an oxygen atom and/or is optionally substituted by a hydroxyl group or a $C_1$-$C_4$ alkoxy group such as methoxy;
  iii) a $C_5$-$C_{12}$ aryl group which is optionally substituted by one or more hydroxyls and/or by one or more $C_1$-$C_4$ alkoxy radicals;
  it being possible for $R_8$ and $R_9$ to form, with the nitrogen which carries them, a heterocycle having from 5 to 8 members, said heterocycle being able to contain one or more oxygen atoms and/or being optionally substituted by a $C_1$-$C_6$ hydrocarbon chain optionally containing one or more radicals selected from hydroxyl or $C_1$-$C_4$ alkoxy;
e) —OR$_4$
f) —C(O)NHR$_4$,
  where $R_4$ denotes a radical selected from —H, a $C_3$-$C_8$ branched or $C_1$-$C_8$ linear saturated alkyl group which is optionally substituted by one or more identical or different groups selected from:
  i) —COOR$_6$, where $R_6$ is as defined above;
  ii) a $C_5$-$C_{12}$ aryl radical,
g) a radical of formula (III)

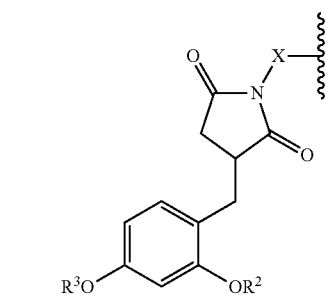

(III)

in which X denotes a $C_3$-$C_8$ cyclic or $C_3$-$C_6$ branched or $C_1$-$C_6$ linear saturated hydrocarbon chain or a $C_6$-$C_{12}$ arylene group such as phenylene, which is optionally substituted by one or more identical or different radicals selected from OH or a $C_1$-$C_6$ alkyl group, $R_2$ and $R_3$ have the same meaning as above;

and when A denotes a radical of formula (III), all of the radicals $R_2$ and $R_3$ in the compounds of formula (II) are identical.

The compounds of formula (I) more preferably have the following meanings:

$R_2$ and $R_3$ independently denote a hydrogen atom or an acetyl group;

A denotes a radical selected from:
a) H
b) a $C_3$-$C_8$ cyclic or $C_3$-$C_{16}$ branched or $C_2$-$C_{16}$ unsaturated or $C_1$-$C_{16}$ linear saturated alkyl group which is optionally interrupted by one or more heteroatoms selected from N and O and/or is optionally substituted by one or more identical or different groups selected from:
  i) —OH
  ii) $C_1$-$C_4$ alkoxy,
  iii) —$CONH_2$;
  iv) —$COOR_6$, where $R_6$ denotes H or a $C_3$-$C_4$ cyclic or $C_2$-$C_4$ unsaturated or $C_3$-$C_4$ branched or $C_1$-$C_4$ linear saturated alkyl group;
  v) a phenyl group which is optionally substituted by one or more hydroxyls and/or by one or more $C_1$-$C_4$ alkoxy radicals;
  vi) a saturated or unsaturated, non-aromatic heterocycle having from 5 to 8 members, comprising one or more nitrogen atoms, it being possible for one of the members to be a carbonyl moiety;
c) a $C_5$-$C_{12}$ aryl group such as phenyl;
d) —$NR_8R_9$, where $R_8$ and $R_9$, which are identical or different, denote H or a $C_3$-$C_8$ cyclic or $C_2$-$C_6$ unsaturated or $C_3$-$C_6$ branched or $C_1$-$C_6$ linear saturated alkyl group; or a $C_5$-$C_{12}$ aryl group such as phenyl;
  it being possible for $R_8$ and $R_9$ to form, with the nitrogen which carries them, a heterocycle having from 5 to 8 members, it being possible for said heterocycle to contain an oxygen atom and/or being optionally substituted by a C1-$C_6$ hydrocarbon chain optionally containing one or more radicals selected from hydroxyl or $C_1$-$C_4$ alkoxy;
e) —$OR_4$, where $R_4$ denotes H or a $C_3$-$C_6$ branched or $C_1$-$C_6$ linear saturated alkyl group which is optionally substituted by one or more identical or different groups selected from:
  i) —COOH,
  ii) a $C_5$-$C_{12}$ aryl radical such as phenyl;
f) a radical of formula (III)

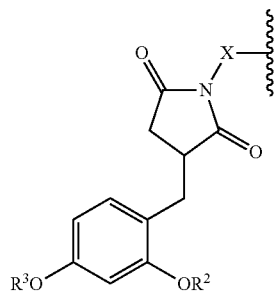

(III)

in which X denotes a $C_3$-$C_8$ cyclic or $C_3$-$C_6$ branched or $C_1$-$C_6$ linear saturated hydrocarbon chain or a $C_6$-$C_{12}$ arylene group such as phenylene, which is optionally substituted by one or more hydroxyl radicals;

$R_2$ and $R_3$ have the same meaning as above;

and when A denotes a radical of formula (III), all of the radicals $R_2$ and $R_3$ in the compounds of formula (II) are identical.

Preferentially, $R_2$ and $R_3$=H for the compounds of formula (II).

A number of embodiments of compounds of formula (II) are described below:

$R_2$ and $R_3$=H, and A=H.

$R_2$ and $R_3$=H, and A=$C_3$-$C_{16}$ branched or $C_1$-$C_{16}$ saturated linear alkyl group.

$R_2$ and $R_3$=H, and A=$C_3$-$C_8$ branched or $C_1$-$C_8$ saturated linear alkyl group which is substituted by one or two hydroxyl groups and is optionally substituted by a group —$SR_5$, where $R_5$=H or $C_1$-$C_4$ alkyl.

$R_2$ and $R_3$=H, and A=phenyl or benzyl group.

$R_2$ and $R_3$=H, and A=$C_3$-$C_8$ branched or $C_1$-$C_8$ alkyl group which is substituted by a phenyl group which is optionally substituted by one or more hydroxyl groups and/or $C_1$-$C_4$ alkoxy group.

$R_2$ and $R_3$=H, and A=$C_3$-$C_8$ branched or $C_1$-$C_8$ saturated linear alkyl group which is substituted by a —COOH group, which is optionally substituted by a group $SR_5$, where $R_5$=H or $C_1$-$C_4$ alkyl.

$R_2$ and $R_3$=H, and A=$C_3$-$C_8$ branched or $C_1$-$C_8$ saturated linear alkyl group which is substituted by a group —$COOR_6$, where $R_6$ denotes a $C_1$-$C_6$ alkyl group, and is optionally substituted by a hydroxyl group and/or a group —$SR_5$, where $R_5$=H or $C_1$-$C_4$ alkyl and/or phenyl which is optionally substituted by one or more hydroxyls, or an imidazole radical.

$R_2$ and $R_3$=H, and A=$C_3$-$C_8$ branched or $C_1$-$C_8$ saturated linear alkyl group which is substituted by a —$CONH_2$ group, which is optionally substituted by a hydroxyl or phenyl group which is optionally substituted by one or more hydroxyls, or a group —$COOR_6$, where $R_6$ denotes a $C_1$-$C_6$ alkyl group.

$R_2$ and $R_3$=H, and A=group —$OR_4$, where $R_4$ denotes H, a $C_3$-$C_6$ branched or $C_1$-$C_6$ linear saturated alkyl group which is optionally substituted by a —COOH group or a phenyl group.

$R_2$ and $R_3$=H, and A=—$NR_8R_9$, where $R_8$ and $R_9$, which are identical or different, denote H or a $C_3$-$C_6$ branched or $C_1$-$C_6$ linear saturated alkyl group or a phenyl group;

it being possible for $R_8$ and $R_9$ to form, with the nitrogen which carries them, a heterocycle which has 5 or 6 members and may contain an oxygen atom, said heterocycle being optionally substituted by a $C_1$-$C_6$ hydrocarbon chain optionally containing one or more radicals selected from hydroxyl or $C_1$-$C_4$ alkoxy.

$R_2$ and $R_3$=H, and A=$C_3$-$C_6$ branched or $C_2$-$C_6$ linear alkyl group interrupted by a —CONH— group and substituted by a COOH group.

$R_2$ and $R_3$=H, and A=$C_5$-$C_6$ cyclic alkyl group interrupted by a —CONH— group.

$R_2$ and $R_3$=H, and A=$C_5$-$C_6$ cyclic alkyl group interrupted by an oxygen atom.

$R_2$ and $R_3$=H, and A=radical of formula (II) as described above in which X denotes a $C_5$-$C_8$ cyclic or $C_3$-$C_6$ branched or $C_1$-$C_6$ linear saturated hydrocarbon chain or a phenylene group, which is optionally substituted by one or more hydroxyl groups.

Among these compounds, more particular preference is given to the following compounds:

| No. | Structure | Chemical name |
|---|---|---|
| 1 | 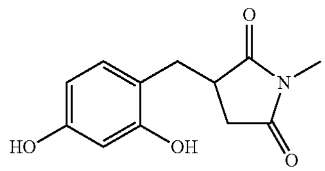 [SMILES: CN1C(=O)CC(Cc2ccc(O)cc2O)C1=O] | 3-(2,4-dihydroxybenzyl)-1-methylpyrrolidine-2,5-dione |
| 2 | 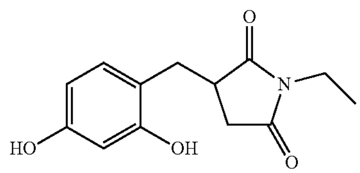 [SMILES: CCN1C(=O)CC(Cc2ccc(O)cc2O)C1=O] | 3-(2,4-dihydroxybenzyl)-1-ethylpyrrolidine-2,5-dione |
| 3 | 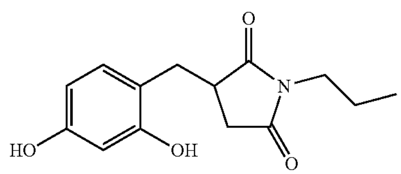 [SMILES: CCCN1C(=O)CC(Cc2ccc(O)cc2O)C1=O] | 3-(2,4-dihydroxybenzyl)-1-propylpyrrolidine-2,5-dione |
| 4 | 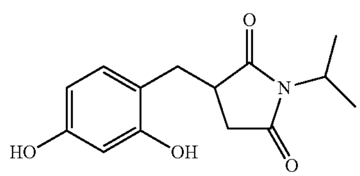 [SMILES: CC(C)N1C(=O)CC(Cc2ccc(O)cc2O)C1=O] | 3-(2,4-dihydroxybenzyl)-1-isopropylpyrrolidine-2,5-dione |
| 5 | 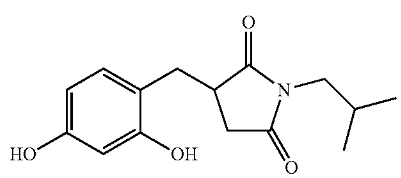 [SMILES: CC(C)CN1C(=O)CC(Cc2ccc(O)cc2O)C1=O] | 3-(2,4-dihydroxybenzyl)-1-isobutylpyrrolidine-2,5-dione |
| 6 | 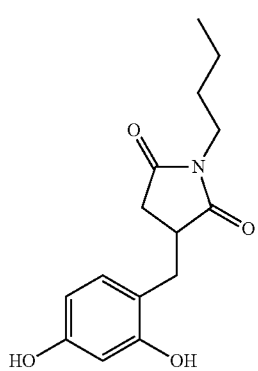 [SMILES: CCCCN1C(=O)CC(Cc2ccc(O)cc2O)C1=O] | 3-(2,4-dihydroxybenzyl)-1-butylpyrrolidine-2,5-Dione |

-continued

| No. | Structure | Chemical name |
|---|---|---|
| 7 | 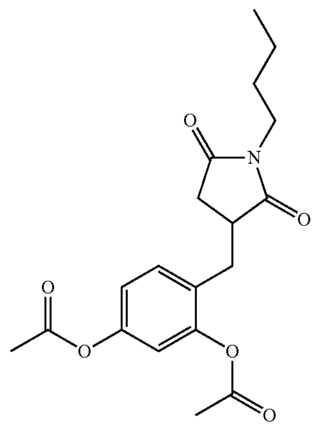 [SMILES: CCCCN1C(=O)CC(Cc2ccc(OC(C)=O)cc2OC(C)=O)C1=O] | 4-[(1-butyl-2,5-dioxopyrrolidin-3-yl)methyl]benzene-1,3-diyl diacetate |
| 8 | 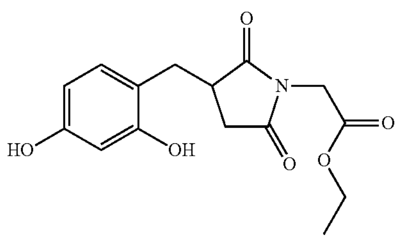 [SMILES: CCOC(=O)CN1C(=O)CC(Cc2ccc(O)cc2O)C1=O] | ethyl [3-(2,4-dihydroxybenzyl)-2,5-dioxopyrrolidin-1-yl]acetate |
| 9 | 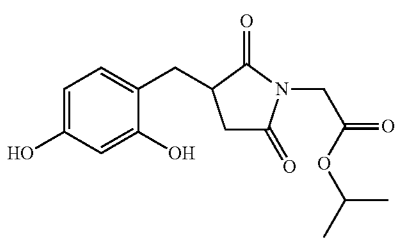 [SMILES: CC(C)OC(=O)CN1C(=O)CC(Cc2ccc(O)cc2O)C1=O] | isopropyl [3-(2,4-dihydroxybenzyl)-2,5-dioxopyrrolidin-1-yl]acetate |
| 10 | 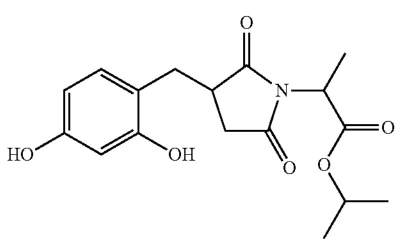 [SMILES: CC(C)OC(=O)C(C)N1C(=O)CC(Cc2ccc(O)cc2O)C1=O] | ethyl 2-[3-(2,4-dihydroxybenzyl)-2,5-dioxopyrrolidin-1-yl]propanoate |
| 11 | | ethyl 2-[3-(2,4-dihydroxybenzyl)-2,5-dioxopyrrolidin-1-yl]-3-methylbutanoate | and also their salts, their solvates, their optical isomers and their racemates.

The above compounds can be prepared in accordance with, for example, the process described in WO 2012/079938, the entirety of which is incorporated herein by reference.

In an embodiment, it may be preferable for the composition in the form of a nano- or macro-emulsion that the ingredient (c) is not resorcinol, butyl resorcinol, or phenylethyl resorcinol.

The amount of the ingredient (c) is not limited, and may range from 0.01 to 15% by weight, preferably from 0.1 to 10% by weight, more preferably from 0.15 to 7% by weight, further more preferably from 0.2 to 5% by weight, and even more preferably from 0.3 to 3% by weight, relative to the total weight of the composition.

[Water]

The composition according to the present invention comprises (d) water.

The amount of (d) water is not limited, and may be from 50 to 99% by weight, preferably from 50 to 95% by weight, and more preferably 60 to 90% by weight, relative to the total weight of the composition.

[Additional Surfactant]

The composition according to the present invention may further comprise at least one nonionic surfactant different from the above ingredient (b) and/or at least one additional ionic surfactant. A single type of additional surfactant may be used, but two or more different types of additional surfactant may be used in combination. The ionic surfactant can be selected from cationic surfactants, anionic surfactants, and amphoteric surfactants.

(Nonionic Surfactant)

The additional nonionic surfactant is not limited as long as it is different from the above (b) polyglyceryl fatty acid ester.

The additional nonionic surfactant may have an HLB value of from 8.0 to 14.0, preferably from 9.0 to 13.5, and more preferably from 9.5 to 13.0. If two or more additional nonionic surfactants are used, the HLB value is determined by the weight average of the HLB values of all the additional nonionic surfactants.

The HLB is the ratio between the hydrophilic part and the lipophilic part in the molecule. This term HLB is well known to those skilled in the art and is described in "The HLB system. A time-saving guide to emulsifier selection" (published by ICI Americas Inc., 1984).

The term HLB ("hydrophilic-lipophilic balance") is well known to those skilled in the art, and denotes the hydrophilic-lipophilic balance of a surfactant.

The HLB or hydrophilic-lipophilic balance of the surfactant(s) used according to the invention is the HLB according to Griffin, defined in the publication *J. Soc. Cosm. Chem.*, 1954 (Vol 5), pages 249-256 or the HLB determined experimentally and as described in the publication from the authors F. Puisieux and M. Seiller, entitled "Galenica 5: Les systèmes dispersés [Dispersed systems]—Volume I—Agents de surface et émulsions [Surface agents and emulsions]—Chapter IV—Notions de HLB et de HLB critique [Notions of HLB and of critical HLB], pages 153-194—paragraph 1.1.2. Détermination de HLB par voie expérimentale [Experimental determination of HLB], pages 164-180.

It is preferably the calculated HLB values that should be taken into account.

The calculated HLB is defined as being the following coefficient: calculated HLB=20×molar mass of the hydrophilic part/total molar mass.

For an oxyethylenated fatty alcohol, the hydrophilic part corresponds to the oxyethylene units fused to the fatty alcohol and the calculated HLB then corresponds to the HLB according to Griffin (Griffin W. C., J. Soc. Cosmet. Chemists, 5, 249, 1954).

The (b) nonionic surfactant with an HLB value of from 8.0 to 14.0, preferably from 9.0 to 13.5, and more preferably from 9.5 to 13.0 may be chosen from:

(1) silicone surfactants, (2) surfactants that are fluid at a temperature of less than or equal to 45° C., chosen from the esters of at least one polyol chosen from the group formed by polyethylene glycol comprising from 1 to 60 ethylene oxide units, sorbitan, glycerol comprising from 2 to 30 ethylene oxide units, polyglycerols comprising from 2 to 10 glycerol units, and of at least one fatty acid comprising at least one saturated or unsaturated, linear or branched $C_8$-$C_{22}$ alkyl chain, (3) mixed esters of fatty acid or of fatty alcohol, of carboxylic acid and of glycerol, (4) fatty acid esters of sugars and fatty alcohol ethers of sugars, (5) surfactants that are solid at a temperature of less than or equal to 45° C., chosen from fatty esters of glycerol, fatty esters of sorbitan and oxyethylenated fatty esters of sorbitan, ethoxylated fatty ethers and ethoxylated fatty esters, and (6) block copolymers of ethylene oxide (A) and of propylene oxide (B).

As silicone surfactants which can be used according to the present invention, mention may be made of those disclosed in documents U.S. Pat. Nos. 5,364,633 and 5,411,744.

The (1) silicone surfactant as the above nonionic surfactant may preferably be a compound of formula (I):

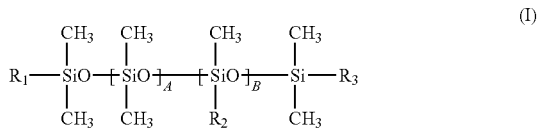

in which:

$R_1$, $R_2$ and $R_3$, independently of each other, represent a $C_1$-$C_6$ alkyl radical or a radical —$(CH_2)_x$—$(OCH_2CH_2)_y$—$(OCH_2CH_2CH_2)_z$—$OR_4$, at least one radical $R_1$, $R_2$ or $R_3$ not being an alkyl radical;

$R_4$ being a hydrogen, an alkyl radical or an acyl radical;

A is an integer ranging from 0 to 200;

B is an integer ranging from 0 to 50; with the proviso that A and B are not simultaneously equal to zero;

x is an integer ranging from 1 to 6;

y is an integer ranging from 1 to 30;

z is an integer ranging from 0 to 5.

According to one preferred embodiment of the invention, in the compound of formula (I), the alkyl radical is a methyl radical, x is an integer ranging from 2 to 6 and y is an integer ranging from 4 to 30.

As examples of silicone surfactants of formula (I), mention may be made of the compounds of formula (II):

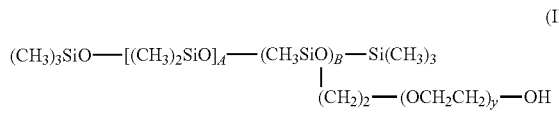

in which A is an integer ranging from 20 to 105, B is an integer ranging from 2 to 10 and y is an integer ranging from 10 to 20.

As examples of silicone surfactants of formula (I), mention may also be made of the compounds of formula (III):

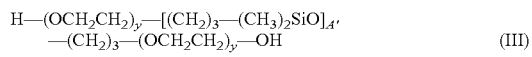

in which A' and y are integers ranging from 10 to 20.

Compounds of the invention which may be used are those sold by the company Dow Corning under the names DC 5329, DC 7439-146, DC 2-5695 and Q4-3667. The compounds DC 5329, DC 7439-146 and DC 2-5695 are compounds of formula (II) in which, respectively, A is 22, B is 2 and y is 12; A is 103, B is 10 and y is 12; A is 27, B is 3 and y is 12.

The compound Q4-3667 is a compound of formula (III) in which A is 15 and y is 13.

The (2) surfactants that are fluid at a temperature of less than or equal to 45° C. may be, in particular:
  the isostearate of polyethylene glycol of molecular weight 400, sold under the name PEG 400 by the company Unichema;
  diglyceryl isostearate, sold by the company Solvay;
  glyceryl laurate comprising 2 glycerol units, sold by the company Solvay;
  sorbitan oleate, sold under the name Span 80 by the company ICI;
  sorbitan isostearate, sold under the name Nikkol SI 10R by the company Nikko; and
  α-butylglucoside cocoate or α-butylglucoside caprate, sold by the company Ulice.

The (3) mixed esters of fatty acid or of fatty alcohol, of carboxylic acid and of glycerol, which can be used as the above nonionic surfactant, may be chosen in particular from the group comprising mixed esters of fatty acid or of fatty alcohol with an alkyl chain containing from 8 to 22 carbon atoms, and of α-hydroxy acid and/or of succinic acid, with glycerol. The α-hydroxy acid may be, for example, citric acid, lactic acid, glycolic acid or malic acid, and mixtures thereof.

The alkyl chain of the fatty acids or alcohols from which are derived the mixed esters which can be used in the nanoemulsion of the invention may be linear or branched, and saturated or unsaturated. They may especially be stearate, isostearate, linoleate, oleate, behenate, arachidonate, palmitate, myristate, laurate, caprate, isostearyl, stearyl, linoleyl, oleyl, behenyl, myristyl, lauryl or capryl chains, and mixtures thereof.

As examples of mixed esters which can be used in the nanoemulsion of the invention, mention may be made of the mixed ester of glycerol and of the mixture of citric acid, lactic acid, linoleic acid and oleic acid (CTFA name: Glyceryl citrate/lactate/linoleate/oleate) sold by the company Hüls under the name Imwitor 375; the mixed ester of succinic acid and of isostearyl alcohol with glycerol (CTFA name: Isostearyl diglyceryl succinate) sold by the company Hills under the name Imwitor 780 K; the mixed ester of citric acid and of stearic acid with glycerol (CTFA name: Glyceryl stearate citrate) sold by the company Hüls under the name Imwitor 370; the mixed ester of lactic acid and of stearic acid with glycerol (CTFA name: Glyceryl stearate lactate) sold by the company Danisco under the name Lactodan B30 or Rylo LA30.

The (4) fatty acid esters of sugars, which can be used as the above nonionic surfactant, may preferably be solid at a temperature of less than or equal to 45° C. and may be chosen in particular from the group comprising esters or mixtures of esters of $C_8$-$C_{22}$ fatty acid and of sucrose, of maltose, of glucose or of fructose, and esters or mixtures of esters of $C_{14}$-$C_{22}$ fatty acid and of methylglucose.

The $C_8$-$C_{22}$ or $C_{14}$-$C_{22}$ fatty acids forming the fatty unit of the esters which can be used in the present invention comprise a saturated or unsaturated linear alkyl chain containing, respectively, from 8 to 22 or from 14 to 22 carbon atoms. The fatty unit of the esters may be chosen in particular from stearates, behenates, arachidonates, palmitates, myristates, laurates and caprates, and mixtures thereof. Stearates are preferably used.

As examples of esters or mixtures of esters of fatty acid and of sucrose, of maltose, of glucose or of fructose, mention may be made of sucrose monostearate, sucrose distearate and sucrose tristearate and mixtures thereof, such as the products sold by the company Croda under the name Crodesta F50, F70, F110 and F160; and examples of esters or mixtures of esters of fatty acid and of methylglucose which may be mentioned are methylglucose polyglyceryl-3 distearate, sold by the company Goldschmidt under the name Tego-care 450. Mention may also be made of glucose or maltose monoesters such as methyl o-hexadecanoyl-6-D-glucoside and o-hexadecanoyl-6-D-maltoside.

The (4) fatty alcohol ethers of sugars, which can be used as the above nonionic surfactant, may be solid at a temperature of less than or equal to 45° C. and may be chosen in particular from the group comprising ethers or mixtures of ethers of $C_8$-$C_{22}$ fatty alcohol and of glucose, of maltose, of sucrose or of fructose, and ethers or mixtures of ethers of a $C_{14}$-$C_{22}$ fatty alcohol and of methylglucose. These are in particular alkylpolyglucosides.

The $C_8$-$C_{22}$ or $C_{14}$-$C_{22}$ fatty alcohols forming the fatty unit of the ethers which may be used in the nanoemulsion of the invention comprise a saturated or unsaturated, linear alkyl chain containing, respectively, from 8 to 22 or from 14 to 22 carbon atoms. The fatty unit of the ethers may be chosen in particular from decyl, cetyl, behenyl, arachidyl, stearyl, palmityl, myristyl, lauryl, capryl and hexadecanoyl units, and mixtures thereof; such as cetearyl.

As examples of fatty alcohol ethers of sugars, mention may be made of alkylpolyglucosides such as decylglucoside and laurylglucoside, which is sold, for example, by the company Henkel under the respective names Plantaren 2000 and Plantaren 1200, cetostearyl glucoside optionally as a mixture with cetostearyl alcohol, sold for example, under the name Montanov 68 by the company SEPPIC, under the name Tego-care CG90 by the company Goldschmidt and under the name Emulgade KE3302 by the company Henkel, as well as arachidyl glucoside, for example in the form of a mixture of arachidyl alcohol and behenyl alcohol and arachidyl glucoside, sold under the name Montanov 202 by the company SEPPIC.

The surfactant used more particularly is sucrose monostearate, sucrose distearate or sucrose tristearate and mixtures thereof; methylglucose polyglyceryl-3 distearate and alkylpolyglucosides.

The (5) fatty esters of glycerol which may be used as the above nonionic surfactant, which are solid at a temperature of less than or equal to 45° C., may be chosen in particular from the group comprising esters formed from at least one acid comprising a saturated linear alkyl chain containing from 16 to 22 carbon atoms and from 1 to 10 glycerol units. One or more of these fatty esters of glycerol may be used in the present invention.

These esters may be chosen in particular from stearates, behenates, arachidates and palmitates, and mixtures thereof. Stearates and palmitates are preferably used.

As examples of surfactants which can be used in the present invention, mention may be made of decaglyceryl monostearate, distearate, tristearate and pentastearate (CTFA names: Polyglyceryl-10 stearate, Polyglyceryl-10 distearate, Polyglyceryl-10 tristearate, Polyglyceryl-10 pentastearate), such as the products sold under the respective names Nikkol Decaglyn 1-S, 2-S, 3-S and 5-S by the company Nikko, and diglyceryl monostearate (CTFA name: Polyglyceryl-2 stearate), such as the product sold by the company Nikko under the name Nikkol DGMS.

The (5) fatty esters of sorbitan which may be used as the above nonionic surfactant, which are solid at a temperature of less than or equal to 45° C., may be chosen from the group comprising $C_{16}$-$C_{22}$ fatty acid esters of sorbitan and oxyethylenated $C_{16}$-$C_{22}$ fatty acid esters of sorbitan. They are formed from at least one fatty acid comprising at least one saturated linear alkyl chain containing, respectively, from 16 to 22 carbon atoms, and from sorbitol or from ethoxylated sorbitol. The oxyethylenated esters generally comprise from 1 to 100 ethylene glycol units and preferably from 2 to 40 ethylene oxide (EO) units.

These esters may be chosen in particular from stearates, behenates, arachidates, palmitates, and mixtures thereof. Stearates and palmitates are preferably used.

As examples of the above nonionic surfactant that can be used in the present invention, mention may be made of sorbitan monostearate (CTFA name: Sorbitan stearate), sold by the company ICI under the name Span 60, sorbitan monopalmitate (CTFA name: Sorbitan palmitate), sold by the company ICI under the name Span 40, and sorbitan tristearate 20 EO (CTFA name: Polysorbate 65), sold by the company ICI under the name Tween 65.

The (5) ethoxylated fatty ethers that are solid at a temperature of less than or equal to 45° C., which may be used as the above nonionic surfactant, are preferably ethers formed from 1 to 100 ethylene oxide units and from at least one fatty alcohol chain containing from 16 to 22 carbon atoms. The fatty chain of the ethers may be chosen in particular from behenyl, arachidyl, stearyl and cetyl units, and mixtures thereof, such as cetearyl. Examples of ethoxylated fatty ethers which may be mentioned are behenyl alcohol ethers comprising 5, 10, 20 and 30 ethylene oxide units (CTFA names: Beheneth-5, Beheneth-10, Beheneth-20, Beheneth-30), such as the products sold under the names Nikkol BB5, BB10, BB20 and BB30 by the company Nikko, and stearyl alcohol ether comprising 2 ethylene oxide units (CTFA name: Steareth-2), such as the product sold under the name Brij 72 by the company ICI.

The (5) ethoxylated fatty esters that are solid at a temperature of less than or equal to 45° C., which may be used as the above nonionic surfactant, are esters formed from 1 to 100 ethylene oxide units and from at least one fatty acid chain containing from 16 to 22 carbon atoms. The fatty chain in the esters may be chosen in particular from stearate, behenate, arachidate and palmitate units, and mixtures thereof. Examples of ethoxylated fatty esters which may be mentioned are the ester of stearic acid comprising 40 ethylene oxide units, such as the product sold under the name Myrj 52 (CTFA name: PEG-40 stearate) by the company ICI, as well as the ester of behenic acid comprising 8 ethylene oxide units (CTFA name: PEG-8 behenate), such as the product sold under the name Compritol HD5 ATO by the company Gattefosse.

The block copolymers of ethylene oxide (A) and of propylene oxide (B), which may be used as surfactants in the nanoemulsion according to the invention, may be chosen in particular from block copolymers of formula (IV):

$$HO(C_2H_4O)_x(C_3H_6O)_y(C_2H_4O)_zH \quad (IV)$$

in which x, y and z are integers such that x+z ranges from 2 to 100 and y ranges from 14 to 60, and mixtures thereof, and more particularly from the block copolymers of formula (IV) having an HLB value ranging from 8.0 to 14.0.

(Cationic Surfactant)

The cationic surfactant is not limited. The cationic surfactant may be selected from the group consisting of optionally polyoxyalkylenated, primary, secondary or tertiary fatty amine salts, quaternary ammonium salts, and mixtures thereof.

Examples of quaternary ammonium salts that may be mentioned include, but are not limited to: those of general formula (I) below:

wherein $R_1$, $R_2$, $R_3$, and $R_4$, which may be identical or different, are chosen from linear and branched aliphatic radicals comprising from 1 to 30 carbon atoms and optionally comprising heteroatoms such as oxygen, nitrogen, sulfur and halogens. The aliphatic radicals may be chosen, for example, from alkyl, alkoxy, $C_2$-$C_6$ polyoxyalkylene, alkylamide, $(C_{12}$-$C_{22})$alkylamido$(C_2$-$C_6)$alkyl, $(C_{12}$-$C_{22})$alkylacetate and hydroxyalkyl radicals; and aromatic radicals such as aryl and alkylaryl; and $X^-$ is chosen from halides, phosphates, acetates, lactates, $(C_2$-$C_6)$ alkyl sulfates and alkyl- or alkylaryl-sulfonates; quaternary ammonium salts of imidazoline, for instance those of formula (II) below:

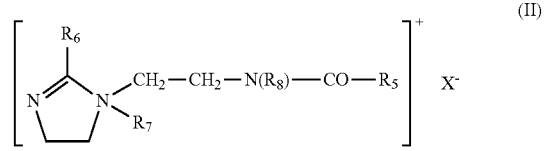

wherein:

$R_5$ is chosen from alkenyl and alkyl radicals comprising from 8 to 30 carbon atoms, for example fatty acid derivatives of tallow or of coconut;

$R_6$ is chosen from hydrogen, $C_1$-$C_4$ alkyl radicals, and alkenyl and alkyl radicals comprising from 8 to 30 carbon atoms;

$R_7$ is chosen from $C_1$-$C_4$ alkyl radicals;

$R_8$ is chosen from hydrogen and $C_1$-$C_4$ alkyl radicals; and $X^-$ is chosen from halides, phosphates, acetates, lactates, alkyl sulfates, alkyl sulfonates, and alkylaryl sulfonates. In one embodiment, $R_5$ and $R_6$ are, for example, a mixture of radicals chosen from alkenyl and alkyl radicals comprising from 12 to 21 carbon atoms, such as fatty acid derivatives of tallow, $R_7$ is methyl and $R_8$ is hydrogen. Examples of such products include, but are not limited to, Quaternium-27 (CTFA 1997) and Quaternium-83 (CTFA 1997), which are sold under the names "Rewoquat®" W75, W90, W75PG and W75HPG by the company Witco;

diquaternary ammonium salts of formula (III):

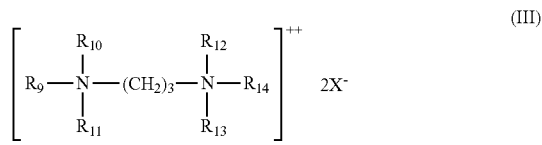

(III)

wherein:

$R_9$ is chosen from aliphatic radicals comprising from 16 to 30 carbon atoms;

$R_{10}$ is chosen from hydrogen or alkyl radicals comprising from 1 to 4 carbon atoms or a group $(R_{16a})(R_{17a})R_{18a})N^+(CH_2)_3$;

$R_{11}$, $R_{12}$, $R_{13}$, $R_{14}$, $R_{16a}$, $R_{17a}$, and $R_{18a}$, which may be identical or different, are chosen from hydrogen and alkyl radicals comprising from 1 to 4 carbon atoms; and $X^-$ is chosen from halides, acetates, phosphates, nitrates, ethyl sulfates, and methyl sulfates.

An example of one such diquaternary ammonium salt is FINQUAT CTP of FINETEX (Quaternium-89) or FINQUAT CT of FINE1EX (Quaternium-75); and quaternary ammonium salts comprising at least one ester function, such as those of formula (IV) below:

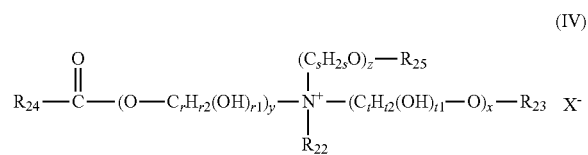

(IV)

wherein:

$R_{22}$ is chosen from $C_1$-$C_6$ alkyl radicals and $C_1$-$C_6$ hydroxyalkyl and dihydroxyalkyl radicals;

$R_{23}$ is chosen from:

the radical below:

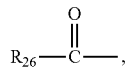

linear and branched, saturated and unsaturated $C_1$-$C_{22}$ hydrocarbon-based radicals $R_{27}$, and hydrogen, $R_{25}$ is chosen from:

the radical below:

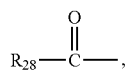

linear and branched, saturated and unsaturated $C_1$-$C_6$ hydrocarbon-based radicals $R_{29}$, and hydrogen, $R_{24}$, $R_{26}$, and $R_{28}$, which may be identical or different, are chosen from linear and branched, saturated and unsaturated, $C_7$-$C_{21}$, hydrocarbon-based radicals;

r, s, and t, which may be identical or different, are chosen from integers ranging from 2 to 6;

each of r1 and t1, which may be identical or different, is 0 or 1, and r2+r1=2r and t1+2t=2t;

y is chosen from integers ranging from 1 to 10;

x and z, which may be identical or different, are chosen from integers ranging from 0 to 10;

$X^-$ is chosen from simple and complex, organic and inorganic anions; with the proviso that the sum x+y+z ranges from 1 to 15, that when x is 0, $R_{23}$ denotes $R_{27}$, and that when z is 0, $R_{25}$ denotes $R_{29}$. $R_{22}$ may be chosen from linear and branched alkyl radicals. In one embodiment, $R_{22}$ is chosen from linear alkyl radicals. In another embodiment, $R_{22}$ is chosen from methyl, ethyl, hydroxyethyl, and dihydroxypropyl radicals, for example methyl and ethyl radicals. In one embodiment, the sum x+y+z ranges from 1 to 10. When $R_{23}$ is a hydrocarbon-based radical $R_{27}$, it may be long and comprise from 12 to 22 carbon atoms, or short and comprise from 1 to 3 carbon atoms. When $R_{25}$ is a hydrocarbon-based radical $R_{29}$, it may comprise, for example, from 1 to 3 carbon atoms. By way of a non-limiting example, in one embodiment, $R_{24}$, $R_{26}$, and $R_{28}$, which may be identical or different, are chosen from linear and branched, saturated and unsaturated, $C_{11}$-$C_{21}$ hydrocarbon-based radicals, for example from linear and branched, saturated and unsaturated $C_{11}$-$C_{21}$ alkyl and alkenyl radicals. In another embodiment, x and z, which may be identical or different, are 0 or 1. In one embodiment, y is equal to 1. In another embodiment, r, s and t, which may be identical or different, are equal to 2 or 3, for example equal to 2. The anion $X^-$ may be chosen from, for example, halides, such as chloride, bromide, and iodide; and $C_1$-$C_4$ alkyl sulfates, such as methyl sulfate. However, methanesulfonate, phosphate, nitrate, tosylate, an anion derived from an organic acid, such as acetate and lactate, and any other anion that is compatible with the ammonium comprising an ester function, are other non-limiting examples of anions that may be used according to the invention. In one embodiment, the anion $X^-$ is chosen from chloride and methyl sulfate.

In another embodiment, the ammonium salts of formula (IV) may be used, wherein:

$R_{22}$ is chosen from methyl and ethyl radicals, x and y are equal to 1;

z is equal to 0 or 1;

r, s and t are equal to 2;

$R_{23}$ is chosen from:

the radical below:

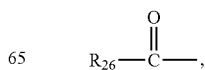

methyl, ethyl, and $C_{14}$-$C_{22}$ hydrocarbon-based radicals, hydrogen;

$R_{25}$ is chosen from:
the radical below:

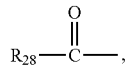

and hydrogen;

$R_{24}$, $R_{26}$, and $R_{28}$, which may be identical or different, are chosen from linear and branched, saturated and unsaturated, $C_{13}$-$C_{17}$ hydrocarbon-based radicals, for example from linear and branched, saturated and unsaturated, $C_{13}$-$C_{17}$ alkyl and alkenyl radicals.

In one embodiment, the hydrocarbon-based radicals are linear.

Non-limiting examples of compounds of formula (IV) that may be mentioned include salts, for example chloride and methyl sulfate, of diacyloxyethyl-dimethylammonium, of diacyloxyethyl-hydroxyethyl-methylammonium, of monoacyloxyethyl-dihydroxyethyl-methylammonium, of triacyloxyethyl-methylammonium, of monoacyloxyethyl-hydroxyethyl-dimethylammonium, and mixtures thereof. In one embodiment, the acyl radicals may comprise from 14 to 18 carbon atoms, and may be derived, for example, from a plant oil, for instance palm oil and sunflower oil. When the compound comprises several acyl radicals, these radicals may be identical or different.

These products may be obtained, for example, by direct esterification of optionally oxyalkylenated triethanolamine, triisopropanolamine, alkyldiethanolamine or alkyldiisopropanolamine onto fatty acids or onto mixtures of fatty acids of plant or animal origin, or by transesterification of the methyl esters thereof. This esterification may be followed by a quaternization using an alkylating agent chosen from alkyl halides, for example methyl and ethyl halides; dialkyl sulfates, for example dimethyl and diethyl sulfates; methyl methanesulfonate; methyl para-toluenesulfonate; glycol chlorohythin; and glycerol chlorohydrin.

Such compounds are sold, for example, under the names Dehyquart® by the company Cognis, Stepanquat® by the company Stepan, Noxamium® by the company Ceca, and "Rewoquat® WE 18" by the company Rewo-Goldschmidt Other non-limiting examples of ammonium salts that may be used in the compositions according to the invention include the ammonium salts comprising at least one ester function described in U.S. Pat. Nos. 4,874,554 and 4,137,180.

Among the quaternary ammonium salts mentioned above that may be used in compositions according to the invention include, but are not limited to, those corresponding to formula (I), for example tetraalkylammonium chlorides, for instance dialkyldimethylammonium and alkyltrimethylammonium chlorides in which the alkyl radical comprises from about 12 to 22 carbon atoms, such as behenyltrimethylammonium, distearyldimethylammonium, cetyltrimethylammonium and benzyldimethylstearylammonium chloride; palmitylamidopropyltrimethylammonium chloride; and stearamidopropyldimethyl(myristyl acetate)ammonium chloride, sold under the name "Ceraphyl® 70" by the company Van Dyk.

According to one embodiment, the cationic surfactant that may be used in the compositions of the invention is chosen from quaternary ammonium salts, for example from behenyltrimethylammonium chloride, cetyltrimethylammonium chloride, Quaternium-83, Quaternium-87, Quaternium-22, behenylamidopropyl-2,3-dihydroxypropyldimethylammonium chloride, palmitylamidopropyltrimethylammonium chloride, and stearamidopropyldimethylamine.

(Anionic Surfactant)

The anionic surfactant is not limited. The anionic surfactant may be chosen in particular from anionic derivatives of proteins of vegetable origin or of silk proteins, phosphates and alkyl phosphates, carboxylates, sulphosuccinates, amino acid derivatives, alkyl sulphates, alkyl ether sulphates, sulphonates, isethionates, taurates, alkyl sulphoacetates, polypeptides, anionic derivatives of alkyl polyglucosides, and their mixtures.

1) Anionic derivatives of proteins of vegetable origin are protein hydrolysates comprising a hydrophobic group, it being possible for the said hydrophobic group to be naturally present in the protein or to be added by reaction of the protein and/or of the protein hydrolysate with a hydrophobic compound. The proteins are of vegetable origin or derived from silk, and the hydrophobic group can in particular be a fatty chain, for example an alkyl chain comprising from 10 to 22 carbon atoms. Mention may more particularly be made, as anionic derivatives of proteins of vegetable origin, of apple, wheat, soybean or oat protein hydrolysates comprising an alkyl chain having from 10 to 22 carbon atoms, and their salts. The alkyl chain can in particular be a lauryl chain and the salt can be a sodium, potassium and/or ammonium salt.

Thus, mention may be made, as protein hydrolysates comprising a hydrophobic group, for example, of salts of protein hydrolysates where the protein is a silk protein modified by lauric acid, such as the product sold under the name Kawa Silk by Kawaken; salts of protein hydrolysates where the protein is a wheat protein modified by lauric acid, such as the potassium salt sold under the name Aminofoam W OR by Croda (CTFA name: potassium lauroyl wheat amino acids) and the sodium salt sold under the name Proteol LW 30 by Seppic (CTFA name: sodium lauroyl wheat amino acids); salts of protein hydrolysates where the protein is an oat protein comprising an alkyl chain having from 10 to 22 carbon atoms and more especially salts of protein hydrolysates where the protein is an oat protein modified by lauric acid, such as the sodium salt sold under the name Proteol OAT (30% aqueous solution) by Seppic (CTFA name: sodium lauroyl oat amino acids); or salts of apple protein hydrolysates comprising an alkyl chain having from 10 to 22 carbon atoms, such as the sodium salt sold under the name Proteol APL (30% aqueous/glycol solution) by Seppic (CTFA name: sodium cocoyl apple amino acids). Mention may also be made of the mixture of lauroyl amino acids (aspartic acid, glutamic acid, glycine, alanine) neutralized with sodium N-methylglycinate sold under the name Proteol SAV 50 S by Seppic (CTFA name: sodium cocoyl amino acids).

2) Mention may be made, as phosphates and alkyl phosphates, for example, of monoalkyl phosphates and dialkyl phosphates, such as lauryl monophosphate, sold under the name MAP 20® by Kao Chemicals, the potassium salt of dodecyl phosphate, the mixture of mono- and diesters (predominantly diester) sold under the name Crafol AP-31® by Cognis, the mixture of octyl phosphate monoester and diester, sold under the name Crafol AP-20® by Cognis, the mixture of ethoxylated (7 mol of EO) 2-butyloctyl phosphate monoester and diester, sold under the name Isofol 12 7 EO-Phosphate Ester® by Condea, the potassium or triethanolamine salt of mono($C_{12}$-$C_{13}$)alkyl phosphate, sold under the references Arlatone MAP 230K-40® and Arlatone MAP 230T-60® by Uniqema, potassium lauryl phosphate, sold under the name Dermalcare MAP XC-99/09® by Rhodia Chimie, and potassium cetyl phosphate, sold under the name Arlatone MAP 160K by Uniqema.

3) Mention may be made, as carboxylates, of
- amido ether carboxylates (AEC), such as sodium lauryl amido ether carboxylate (3 EO), sold under the name Akypo Foam 30® by Kao Chemicals;
- polyoxyethylenated carboxylic acid salts, such as oxyethylenated (6 EO) sodium lauryl ether carboxylate (65/25/10 $C_{12}$-$C_{14}$-$C_{16}$), sold under the name Akypo Soft 45 NV® by Kao Chemicals, polyoxyethylenated and carboxymethylated fatty acids originating from olive oil, sold under the name Olivem 400® by Biologia E Tecnologia, or oxyethylenated (6 EO) sodium tridecyl ether carboxylate, sold under the name Nikkol ECTD-6NEX® by Nikkol; and
- salts of fatty acids (soaps) having a $C_6$ to $C_{22}$ alkyl chain which are neutralized with an organic or inorganic base, such as potassium hydroxide, sodium hydroxide, triethanolamine, N-methylglucamine, lysine and arginine.

4) Mention may in particular be made, as amino acid derivatives, of alkali salts of amino acids, such as:
- sarcosinates, such as sodium lauroyl sarcosinate, sold under the name Sarkosyl NL 97® by Ciba or sold under the name Oramix L 30® by Seppic, sodium myristoyl sarcosinate, sold under the name Nikkol Sarcosinate MN® by Nikkol, or sodium palmitoyl sarcosinate, sold under the name Nikkol Sarcosinate PN® by Nikkol;
- alaninates, such as sodium N-lauroyl-N-methylamidopropionate, sold under the name Sodium Nikkol Alaninate LN 30® by Nikkol or sold under the name Alanone ALE® by Kawaken, or triethanolamine N-lauroyl-N-methylalanine, sold under the name Alanone ALTA® by Kawaken;
- glutamates, such as triethanolamine monococoyl glutamate, sold under the name Acylglutamate CT-12® by Ajinomoto, triethanolamine lauroyl glutamate, sold under the name Acylglutamate LT-12® by Ajinomoto, and sodium stearoyl glutamate;
- aspartates, such as the mixture of triethanolamine N-lauroyl aspartate and triethanolamine N-myristoyl aspartate, sold under the name Asparack® by Mitsubishi;
- glycine derivatives (glycinates), such as sodium N-cocoyl glycinate, sold under the names Amilite GCS-12® and Amilite GCK 12 by Ajinomoto;
- citrates, such as the citric monoester of oxyethylenated (9 mol) coco alcohols, sold under the name Witconol EC 1129 by Goldschmidt; and
- galacturonates, such as sodium dodecyl D-galactoside uronate, sold by Soliance.

5) Mention may be made, as sulphosuccinates, for example, of oxyethylenated (3 EO) lauryl (70/30 $C_{12}$/$C_{14}$) alcohol monosulphosuccinate, sold under the names Setacin 103 Special® and Rewopol SB-FA 30 K 4® by Witco, the disodium salt of a hemisulphosuccinate of $C_{12}$-$C_{14}$ alcohols, sold under the name Setacin F Special Paste® by Zschimmer Schwarz, oxyethylenated (2 EO) disodium oleamidosulphosuccinate, sold under the name Standapol SH 135® by Cognis, oxyethylenated (5 EO) lauramide monosulphosuccinate, sold under the name Lebon A-5000® by Sanyo, the disodium salt of oxyethylenated (10 EO) lauryl citrate monosulphosuccinate, sold under the name Rewopol SB CS 50 by Witco, or ricinoleic monoethanolamide monosulphosuccinate, sold under the name Rewoderm S 1333® by Witco. Use may also be made of polydimethylsiloxane sulphosuccinates, such as disodium PEG-12 dimethicone sulphosuccinate, sold under the name Mackanate-DC 30 by MacIntyre.

6) Mention may be made, as alkyl sulphates, for example, of triethanolamine lauryl sulphate (CTFA name: TEA lauryl sulphate), such as the product sold by Huntsman under the name Empicol TL40 FL or the product sold by Cognis under the name Texapon T42, which products are at 40% in aqueous solution. Mention may also be made of ammonium lauryl sulphate (CTFA name: ammonium lauryl sulphate), such as the product sold by Huntsman under the name Empicol AL 30FL, which is at 30% in aqueous solution.

7) Mention may be made, as alkyl ether sulphates, for example, of sodium lauryl ether sulphate (CTFA name: sodium laureth sulphate), such as that sold under the names Texapon N40 and Texapon AOS 225 UP by Cognis, or ammonium lauryl ether sulphate (CTFA name: ammonium laureth sulphate), such as that sold under the name Standapol EA-2 by Cognis.

8) Mention may be made, as sulphonates, for example, of α-olefinsulphonates, such as sodium α-olefinsulphonate ($C_{14}$-$C_{16}$), sold under the name Bio-Terge AS-40® by Stepan, sold under the names Witconate AOS Protégé® and Sulframine AOS PH 12® by Witco or sold under the name Bio-Terge AS-40 CGS by Stepan, secondary sodium olefinsulphonate, sold under the name Hostapur SAS 30® by Clariant; or linear alkylarylsulphonates, such as sodium xylenesulphonate, sold under the names Manrosol SXS30®, Manrosol SXS40® and Manrosol SXS93® by Manro.

9) Mention may be made, as isethionates, of acylisethionates, such as sodium cocoylisethionate, such as the product sold under the name Jordapon CI P® by Jordan.

10) Mention may be made, as taurates, of the sodium salt of palm kernel oil methyltaurate, sold under the name Hostapon CT Pate® by Clariant; N-acyl-N-methyltaurates, such as sodium N-cocoyl-N-methyltaurate, sold under the name Hostapon LT-SF® by Clariant or sold under the name Nikkol CMT-30-T® by Nikkol, or sodium palmitoyl methyltaurate, sold under the name Nikkol PMT® by Nikkol. The preferred is sodium methyl stearoyl taurate (ex Nikkol SMT Nikkol).

11) The anionic derivatives of alkyl polyglucosides can in particular be citrates, tartrates, sulphosuccinates, carbonates and glycerol ethers obtained from alkyl polyglucosides. Mention may be made, for example, of the sodium salt of cocoylpolyglucoside (1,4) tartaric ester, sold under the name Eucarol AGE-ET® by Cesalpinia, the disodium salt of cocoylpolyglucoside (1,4) sulphosuccinic ester, sold under the name Essai 512 MP® by Seppic, or the sodium salt of cocoylpolyglucoside (1,4) citric ester, sold under the name Eucarol AGE-EC® by Cesalpinia.

It is preferable that the amino acid derivatives be acyl glycine derivatives or glycine derivatives, in particular acyl glycine salt.

The acyl glycine derivatives or glycine derivatives can be chosen from acyl glycine salts (or acyl glycinates) or glycine salts (or glycinates), and in particular from the following.

i) Acyl glycinates of formula (I):

R—HNCH$_2$COOX  (I)

in which
R represents an acyl group R'C=O, with R', which represents a saturated or unsaturated, linear or branched, hydrocarbon chain, preferably comprising from 10 to 30 carbon atoms, preferably from 12 to 22 carbon atoms, preferably from 14 to 22 carbon atoms and better still from 16 to 20 carbon atoms, and X represents a cation chosen, for example, from the ions of alkali metals, such as Na, Li or K, preferably Na or K, the ions of alkaline earth metals, such as Mg, ammonium groups and their mixtures.

The acyl group can in particular be chosen from the lauroyl, myristoyl, behenoyl, palmitoyl, stearoyl, isostearoyl, olivoyl, cocoyl or oleoyl groups and their mixtures.

Preferably, R is a cocoyl or stearoyl group.

ii) Glycinates of following formula (II):

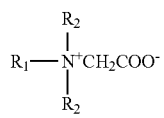

(II)

in which:
- $R_1$ represents a saturated or unsaturated, linear or branched, hydrocarbon chain comprising from 10 to 30 carbon atoms, preferably from 12 to 22 carbon atoms and better still from 16 to 20 carbon atoms; $R_1$ is advantageously chosen from the lauryl, myristyl, palmityl, stearyl, cetyl, cetearyl or oleyl groups and their mixtures and preferably from the stearyl and oleyl groups,
- the $R_2$ groups, which are identical or different, represent an R"OH group, R" being an alkyl group comprising from 2 to 10 carbon atoms, preferably from 2 to 5 carbon atoms.

Mention may be made, as compounds of formula (I), for example, of the compounds carrying the INCI name sodium cocoyl glycinate, such as, for example, Amilite GCS-12, sold by Ajinomoto, or potassium cocoyl glycinate, such as, for example, Amilite GCK-12 from Ajinomoto.

Use may be made, as compounds of formula (II), of dihydroxyethyl oleyl glycinate or dihydroxyethyl stearyl glycinate.

(Amphoteric Surfactant)

The amphoteric surfactant is not limited. The amphoteric or zwitterionic surfactants can be, for example (non-limiting list), amine derivatives such as aliphatic secondary or tertiary amine, and optionally quaternized amine derivatives, in which the aliphatic radical is a linear or branched chain comprising 8 to 22 carbon atoms and containing at least one water-solubilizing anionic group (for example, carboxylate, sulphonate, sulphate, phosphate or phosphonate).

Among the amidoaminecarboxylated derivatives, mention may be made of the products sold under the name Miranol, as described in U.S. Pat. Nos. 2,528,378 and 2,781,354 and classified in the CTFA dictionary, 3rd edition, 1982 (the disclosures of which are incorporated herein by reference), under the names Amphocarboxyglycinates and Amphocarboxypropionates, with the respective structures:

in which:
$R_1$ denotes an alkyl radical of an acid $R_1$—COOH present in hydrolysed coconut oil, a heptyl, nonyl or undecyl radical,
$R_2$ denotes a beta-hydroxyethyl group, and
$R_3$ denotes a carboxymethyl group; and

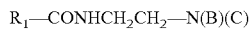

in which:
B represents —CH$_2$CH$_2$OX',
C represents —(CH$_2$)$_z$—Y, with z=1 or 2, X' denotes a —CH$_2$CH$_2$—COOH group, —CH$_2$—COOZ', —CH$_2$CH$_2$—COOH, —CH$_2$CH$_2$—COOZ' or a hydrogen atom, denotes —COOH, —COOZ', —CH$_2$—CHOH—SO$_3$Z' or a —CH$_2$—CHOH—SO$_3$H radical, Z' represents an ion of an alkaline or alkaline earth metal such as sodium, an ammonium ion or an ion issued from an organic amine, and $R_1$' denotes an alkyl radical of an acid $R_1$'—COOH present in coconut oil or in hydrolysed linseed oil, an alkyl radical, such as a $C_7$, $C_9$, $C_{11}$ or $C_{13}$ alkyl radical, a $C_{17}$ alkyl radical and its iso form, or an unsaturated $C_{17}$ radical.

It is preferable that the amphoteric surfactant be selected from $(C_8-C_{24})$-alkyl amphomonoacetates, $(C_8-C_{24})$alkyl amphodiacetates, $(C_8-C_{24})$alkyl amphomonopropionates, and $(C_8-C_{24})$alkyl amphodipropionates These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphopropionate, Disodium Caprylamphodipropionate, Disodium Caprylamphodipropionate, Lauroamphodipropionic acid and Cocoamphodipropionic acid.

By way of example, mention may be made of the cocoamphodiacetate sold under the trade name Miranol® C2M concentrate by the company Rhodia Chimie.

Preferably, the amphoteric surfactant may be a betaine.

The betaine-type amphoteric surfactant is preferably selected from the group consisting of alkylbetaines, alkylamidoalkylbetaines, sulfobetaines, phosphobetaines, and alkylamidoalkylsulfobetaines, in particular, $(C_5-C_{24})$alkylbetaines, $(C_8-C_{24})$alkylamido$(C_1-C_8)$alkylbetaines, sulphobetaines, and $(C_8-C_{24})$alkylamido$(C_1-C_8)$alkylsulphobetaines. In one embodiment, the amphoteric surfactants of betaine type are chosen from $(C_8-C_{24})$alkylbetaines, $(C_8-C_{24})$alkylamido$(C_1-C_8)$alkylsulphobetaines, sulphobetaines, and phosphobetaines.

Non-limiting examples that may be mentioned include the compounds classified in the CTFA dictionary, 9th edition, 2002, under the names cocobetaine, laurylbetaine, cetylbetaine, coco/oleamidopropylbetaine, cocamidopropylbetaine, palmitamidopropylbetaine, stearamidopropylbetaine, cocamidoethylbetaine, cocamidopropylhydroxysultaine, oleamidopropylhydroxysultaine, cocohydroxysultaine, laurylhydroxysultaine, and cocosultaine, alone or as mixtures.

The betaine-type amphoteric surfactant is preferably an alkylbetaine and an alkylamidoalkylbetaine, in particular cocobetaine and cocamidopropylbetaine.

In one embodiment, anionic and cationic surfactants and amphoteric surfactants have a chain longer than $C_{16}$.

The amount of the additional surfactant(s) may be from 0.01 to 15% by weight, preferably from 0.10 to 10% by weight, and more preferably from 0.50 to 5% by weight, relative to the total weight of the composition.

[Polyol]

The composition according to the present invention may further comprise at least one polyol. A single type of polyol may be used, but two or more different types of polyol may be used in combination.

The term "polyol" here means an alcohol having two or more hydroxy groups, and does not encompass a saccharide or a derivative thereof. The derivative of a saccharide includes a sugar alcohol which is obtained by reducing one or more carbonyl groups of a saccharide, as well as a saccharide or a sugar alcohol in which the hydrogen atom or atoms in one or more hydroxy groups thereof has or have been replaced with at least one substituent such as an alkyl group, a hydroxyalkyl group, an alkoxy group, an acyl group or a carbonyl group.

The polyol may be a $C_2$-$C_{12}$ polyol, preferably a $C_{2-9}$ polyol, comprising at least 2 hydroxy groups, and preferably 2 to 5 hydroxy groups.

The polyol may be a natural or synthetic polyol. The polyol may have a linear, branched or cyclic molecular structure.

The polyol may be selected from glycerins and derivatives thereof, and glycols and derivatives thereof.

The polyol may be selected from the group consisting of glycerin, diglycerin, polyglycerin, ethyleneglycol, diethyleneglycol, propyleneglycol, dipropyleneglycol, butyleneglycol, pentyleneglycol, hexyleneglycol, 1,3-propanediol, 1,5-pentanediol, polyethyleneglycol (5 to 50 ethyleneoxide groups), and sugars such as sorbitol.

The polyol may be present in an amount ranging from 0.01 to 20% by weight, preferably from 0.1 to 15% by weight, and more preferably from 1 to 10% by weight, relative to the total weight of the composition.

[Other Ingredients]

The composition according to the invention is advantageously a cosmetic composition.

The composition according to the present invention may also comprise an effective amount of other ingredients, known previously elsewhere in cosmetic compositions, such as various common adjuvants, antiageing agents, whitening agents, anti greasy skin agents, sequestering agents such as EDTA and etidronic acid, UV screening agents, silicones other than those mentioned before (such as with amine groups), preserving agents, vitamins or provitamins, for instance, panthenol, opacifiers, fragrances, plant extracts, cationic polymers and so on.

The composition according to the present invention may further comprise at least one organic solvent. The organic solvent is preferably water miscible. As the organic solvent, there may be mentioned, for example, $C_1$-$C_4$ alkanols, such as ethanol and isopropanol; aromatic alcohols such as benzyl alcohol and phenoxyethanol; analogous products; and mixtures thereof.

The organic water-soluble solvents may be present in an amount ranging from less than 10% by weight, preferably from 5% by weight or less, and more preferably from 1% by weight or less, relative to the total weight of the composition.

[Preparation and Properties]

The composition according to the present invention can be prepared by mixing the above essential and optional ingredients in accordance with a conventional process. The conventional process includes mixing with a high pressure homogenizer (a high energy process). Alternatively, the composition according to the present invention can be prepared by a low energy process such as simple mechanical agitation, phase inversion temperature process (PIT), phase inversion concentration (PIC), autoemulsification, and the like.

[Other Aspects]

The composition according to the present invention can be in the form of a nano- or micro-emulsion, or can have a lamellar structure of a lamellar phase.

The term "micro-emulsion" may be defined in two ways, namely, in a broader sense and in a narrower sense. That is to say, there are one case ("microemulsion in the narrow sense") in which the microemulsion refers to a thermodynamically stable isotropic single liquid phase containing a ternary system having three ingredients of an oily component, an aqueous component and a surfactant, and the other case ("micro-emulsion in the broad sense") in which among thermodynamically unstable typical emulsion systems the microemulsion additionally includes those such emulsions presenting transparent or translucent appearances due to their smaller particle sizes (Satoshi Tomomasa, et al., Oil-Chemistry, Vol. 37, No. 11 (1988), pp. 48-53). The term "micro-emulsion" as used herein refers to a "micro-emulsion in the narrow sense," i.e., a thermodynamically stable isotropic single liquid phase.

The term micro-emulsion refers to either one state of an O/W (oil-in-water) type microemulsion in which oil is solubilized by micelles, a W/O (water-in-oil) type microemulsion in which water is solubilized by reverse micelles, or a bicontinuous microemulsion in which the number of associations of surfactant molecules are rendered infinite so that both the aqueous phase and oil phase have a continuous structure.

The micro-emulsion may have a dispersed phase with a number average diameter of 250 nm or less, preferably 200 nm or less, and more preferably 150 nm or less, measured by laser granulometry.

The term "nano-emulsion" here means an emulsion characterized by a dispersed phase with a size of 250 nm or less, the dispersed phase being stabilized by a crown of the (b) polyglyceryl fatty acid ester and the like. In the absence of specific opacifiers, the transparency of the nano-emulsions arises from the small size of the dispersed phase, this small size being obtained by virtue of the use of mechanical energy and especially a high-pressure homogenizer.

Nanoemulsions can be distinguished from microemulsions by their structure. Specifically, micro-emulsions are thermodynamically stable dispersions formed from, for example, micells which are formed by the (b) polyglyceryl fatty acid ester micells and the like and are swollen with the (a) oil. Furthermore, microemulsions do not require substantial mechanical energy in order to be prepared.

The nano-emulsion may have a dispersed phase with a number average diameter of 250 nm or less, preferably 200 nm or less, and more preferably 150 nm or less, measured by laser granulometry.

The composition according to the present invention may be in the form of an O/W nano- or micro-emulsion, a W/O nano- or micro-emulsion or a bicontinuous emulsion. It is preferable that the composition according to the present invention be in the form of an O/W nano- or micro-emulsion.

It is preferable that the composition according to the present invention be in the form of an O/W emulsion, and the (a) oil be in the form of a droplet with a number average particle size of 250 nm or less, preferably from 10 nm to 200 nm, and more preferably 20 nm to 150 nm. The number average particle size can be measured, for example, by a VASCO-2 (CORDOUAN TECHNOLOGIES) under non-diluted conditions. A computer program makes it possible to obtain the mean diameter by specifying intensity.

The composition according to the present invention can have a lamellar structure or a lamellar phase. As mentioned above, the term "lamellar structure" or "lamellar phase" means a liquid crystal structure or phase with plane symmetry, comprising several amphiphilic bilayers arranged in parallel and separated by a liquid medium which is generally water. A combination of the ingredients (b) and (c) can contribute to form a lamellar structure or a lamellar phase. In one embodiment, a lamellar structure or a lamellar phase may be present at the dispersed phase/continuous phase interface, such as the interface between the (a) oil and the (d) water. In this case, the composition according to the present invention may be in the form of a nano- or micro-emulsion with a lamellar structure or a lamellar phase.

The composition according to the present invention can have a transparent or slightly translucent appearance, preferably a transparent appearance.

Polarization when being observed via a polarization plate can be visually evaluated. If polarization is observed, this means that lamellar structure is formed.

The transparency may be measured by measuring the transmittance with absorption spectrometer in the visible region (for example, a V-550 (JASCO) with a 2 mm width cell as an average of visible light transmittance (between 400 and 800 nm). The measurement is taken on the undiluted composition. The blank is determined with distilled water.

The composition according to the present invention may preferably have a transparency greater than 50%, preferably greater than 60%, and more preferably greater than 70%, and even more preferably greater than 80%.

[Process and Use]

The composition according to the present invention can be used for a non-therapeutic process, such as a cosmetic process, for treating the skin, the hair, mucous membranes, the nails, the eyelashes, the eyebrows and/or the scalp, by being applied to the skin, the hair, mucous membranes, the nails, the eyelashes, the eyebrows or the scalp.

The present invention also relates to a use of the composition according to the present invention, as it is or in care products and/or washing products and/or make-up products and/or make-up-removing products for body and/or facial skin and/or mucous membranes and/or the scalp and/or the hair and/or the nails and/or the eyelashes and/or the eyebrows.

In other words, the composition according to the present invention can be used, as it is, as the above product. Alternatively, the composition according to the present invention can be used as an element of the above product. For example the composition according to the present invention can be added to or combined with any other elements to form the above product.

The care product may be a lotion, a cream, a hair tonic, a hair conditioner, a sun screening agent, and the like. The washing product may be a shampoo, a face wash, a hand wash and the like. The make-up product may be a foundation, a mascara, a lipstick, a lip gloss, a blusher, an eye shadow, a nail varnish, and the like. The make-up-removing product may be a make-up cleansing agent and the like.

EXAMPLES

The present invention will be described in more detail by way of examples, which however should not be construed as limiting the scope of the present invention.

(Aspect) Aspect was determined based on visual evaluation.

(Transparency) Transparency was measured with a V-550 (JASCO) with 2 mm width cell as an average of visible light transmittance (between 400 and 800 nm).

(Particle Size) Particle size was measured with a VASCO-2 (CORDOUAN TECHNOLOGIES) with non-diluted condition. A computer program makes it possible to obtain the mean diameter by specifying intensity.

(Lamellar Structure) Polarization when being observed via a polarization plate (KENIS LTD.) was visually evaluated. If polarization was observed, this means that lamellar structure was formed.

Examples 1 and 2, and Comparative Example 1

The following compositions according to Examples 1 and 2, and Comparative Example 1, shown in Table 1, were prepared by mixing the components shown in Table 1 as follows: (1) mixing polyglyceryl-5 oleate, dicaprylyl carbonate, and phenylethyl resorcinol, if used, to form an oil phase; (2) heating the oil phase up to around 75° C.; (3) heating water up to around 75° C. to form an aqueous phase; (4) adding the aqueous phase into the oil phase followed by mixing them to obtain an O/W emulsion by phase inversion concentration (PIC); and (5) cooling the O/W emulsion down to room temperature. The numerical values for the amounts of the components shown in Table 1 are all based on "% by weight" as active raw materials.

TABLE 1

|  | Example 1 | Example 2 | Comparative Example 1 |
| --- | --- | --- | --- |
| Polyglyceryl-5 Oleate* (HLB: 12.7) | 7.50% | 7.50% | 7.50% |
| Dicaprylyl Carbonate | 15.00% | 15.00% | 15.00% |
| Phenylethyl Resorcinol** | 0.50% | 0.75% | — |
| Water | q.s. 100% | q.s. 100% | q.s. 100% |

*SUNSOFT A-171E-C (Taiyo Kagaku)
**SYMWHITE 377 (Symrise)

The aspect, transparency, and particle size of oil droplets of the obtained emulsions according to Examples 1 and 2, and Comparative Example 1 are shown in Table 2.

TABLE 2

|  | Example 1 | Example 2 | Comparative Example 1 |
| --- | --- | --- | --- |
| Aspect | Slightly Hazy Transparent | Translucent | White |
| Transparency (%) | 82.2 | 73.9 | 35.4 |
| Particle size (nm) | 127 | 121 | 447 |

Example 3 and Comparative Example 2

The following compositions according to Example 3 and Comparative Example 2, shown in Table 3, were prepared by mixing the components shown in Table 3 as follows: (1) mixing polyglyceryl-5 oleate, dicaprylyl carbonate, and 4-(tetrahydro-2H-pyran-4-yl)benzene-1,3-diol, if used, to form an oil phase; (2) heating the oil phase up to around 75° C.; (3) heating water up to around 75° C. to form an aqueous phase; (4) adding the aqueous phase into the oil phase followed by mixing them to obtain an O/W emulsion by phase inversion concentration (PIC); and (5) cooling the O/W emulsion down to room temperature. The numerical values for the amounts of the components shown in Table 3 are all based on "% by weight" as active raw materials.

TABLE 3

|  | Example 3 | Comparative Example 2 |
| --- | --- | --- |
| Polyglyceryl-5 Oleate* (HLB: 12.7) | 7.50% | 7.50% |
| Dicaprylyl Carbonate | 15.00% | 15.00% |
| 4-(Tetrahydro-2H-pyran-4-yl)benzene-1,3-diol | 0.30% | — |
| Water | q.s. 100% | q.s. 100% |

*SUNSOFT A-171E-C (Taiyo Kagaku)

The aspect and transparency of the obtained micro/nano O/W emulsions according to Example 3 and Comparative Example 2 are shown in Table 4.

TABLE 4

|  | Example 3 | Comparative Example 2 |
|---|---|---|
| Aspect | Translucent | White |
| Transparency (%) | 67.2 | 35.4 |

As is clear from the above results, it was found that the composition in the form of a micro/nano O/W emulsion according to the present invention had smaller oil droplets, and therefore, provided a more transparent or translucent aspect with better transparency, due to the presence of a resorcinol derivative in the composition.

Example 4 and Comparative Examples 3 and 4

The following compositions according to Example 4 and Comparative Examples 3 and 4, shown in Table 5, were prepared by mixing the components shown in Table 5 as follows: (1) mixing polyglyceryl-5 oleate or oleth-10, polyglyceryl-2 caprate or sorbitan caprylate, phenylethyl resorcinol, if used, isopropyl lauroyl sarcosinate, phenoxyethanol, and caprylyl glycol to form an oil phase; (2) heating the oil phase up to around 75° C.; (3) mixing sodium methyl stearoyl taurate, glycerin, butyleneglycol and water to form an aqueous phase; (4) heating the aqueous phase up to around 75° C.; (5) adding the aqueous phase into the oil phase followed by mixing them to obtain a viscous liquid by phase inversion concentration (PIC); and (6) cooling the viscous liquid down to room temperature. The numerical values for the amounts of the components shown in Table 5 are all based on "% by weight" as active raw materials.

TABLE 5

|  | Example 4 | Comparative Example 3 | Comparative Example 4 |
|---|---|---|---|
| Polyglyceryl-5 Oleate* (HLB: 12.7) | 5.50% | 5.50% | — |
| Polyglyceryl-2 Caprate*** (HLB: 9.5) | 1.50% | 1.50% | — |
| Oleth-10**** (HLB: 12.4) | — | — | 5.50% |
| Sorbitan Caprylate***** (HLB: 9.6) | — | — | 1.50% |
| Phenylethyl Resorcinol** | 0.30% | — | 0.30% |
| Isopropyl Lauroyl Sarcosinate | 1.00% | 1.00% | 1.00% |
| Phenoxyethanol | 0.70% | 0.70% | 0.70% |
| Caprylyl Glycol | 0.30% | 0.30% | 0.30% |
| Sodium Methyl Stearoyl Taurate | 0.20% | 0.20% | 0.20% |
| Glycerin | 3.00% | 3.00% | 3.00% |
| Butyleneglycol | 2.50% | 2.50% | 2.50% |
| Water | q.s. 100% | q.s. 100% | q.s. 100% |

*SUNSOFT A-171E-C (Taiyo Kagaku)
**SYMWHITE 377 (Symrise)
***SUNSOFT Q-10D-C (Taiyo Kagaku)
****BRIJ O10 (Croda)
*****NONION CP-08R (NOF Corporation)

The aspect, transparency and formation of a lamellar structure of the obtained viscous liquid according to Example 4 and Comparative Examples 3 and 4 are shown in Table 6.

TABLE 6

|  | Example 4 | Comparative Example 3 | Comparative Example 4 |
|---|---|---|---|
| Aspect | Transparent Gel | Slightly Hazy Transparent | Hazy to White |
| Transparency (%) | 91.00 | 82.60 | 6.72 |
| Lamellar Structure | Formed | Formed | Formed |

The viscous liquid according to Example 4 easily became fluid on the skin. Thus, the composition according to Example 4 had good spreadability on the skin, while providing a good feeling to use such as a water-like fresh feeling to the touch.

Example 5 and Comparative. Example 5

The following compositions according to Example 5 and Comparative Example 5, shown in Table 7, were prepared by mixing the components shown in Table 7 as follows: (1) mixing polyglyceryl-5 laurate, isopropyl myristate, and tocopherol to form an oil phase; (2) heating the oil phase up to around 75° C.; (3) mixing 4-(tetrahydro-2H-pyran-4-yl)benzene-1,3-diol, if used, sodium methyl stearoyl taurate, sodium stearoyl glutamate, dimethyl isosorbide, phenoxyethanol, chlorphenesin, butyleneglycol, propyleneglycol, disodium EDTA, citric acid and water to form an aqueous phase; (4) heating the aqueous phase up to around 75° C.; (5) adding the aqueous phase into the oil phase followed by mixing them to obtain a viscous liquid by phase inversion concentration (PIC); and (6) cooling the viscous liquid down to room temperature. The numerical values for the amounts of the components shown in Table 7 are all based on "% by weight" as active raw materials.

TABLE 7

|  | Example 5 | Comparative Example 5 |
|---|---|---|
| Polyglyceryl-5 Laurate****** (HLB: 10.9) | 5.00% | 5.00% |
| Isopropyl Myristate | 3.00% | 3.00% |
| Tocopherol | 0.10% | 0.10% |
| 4-(Tetrahydro-2H-pyran-4-yl)benzene-1,3-diol | 0.50% | — |
| Sodium Mehyl Stearoyl Taurate | 0.30% | 0.30% |
| Sodium Stearoyl Glutamate | 0.30% | 0.30% |
| Dimethyl Isosorbide | 1.00% | 1.00% |
| Phenoxyethanol | 0.50% | 0.50% |
| Chlorphenesin | 0.50% | 0.50% |
| Butyleneglycol | 3.00% | 3.00% |
| Propyleneglycol | 9.50% | 9.50% |
| Disodium EDTA | 0.10% | 0.10% |
| Citric Acid | 0.10% | 0.10% |
| Water | q.s. 100% | q.s. 100% |

******SUNSOFT A-121E-C (Taiyo Kagaku)

The aspect, transparency and formation of a lamellar structure of the obtained viscous liquid according to Example 5 and Comparative Example 5 are shown in Table 8.

TABLE 8

|  | Example 5 | Comparative Example 5 |
|---|---|---|
| Aspect | Translucent | Translucent |
| Transparency (%) | 78.39 | 68.60 |
| Lamellar Structure | Formed | Not Formed |

Example 6 and Comparative Example 6

The following compositions according to Example 6 and Comparative Example 6, shown in Table 9, were prepared by mixing the components shown in Table 9 as follows: (1) mixing polyglyceryl-5 laurate, polyglyceryl-2 caprate, and isopropyl myristate to form an oil phase; (2) heating the oil phase up to around 75° C.; (3) mixing butyleneglycol, phenoxyethanol, caprylyl glycol, 3-(2,4-dihydroxybenzyl)1-(2-hydroxyethyl)pyrrolidine-2,5-dione, if used, and water to form an aqueous phase; (4) heating the aqueous phase up to around 75° C.; (5) adding the aqueous phase into the oil phase followed by mixing them to obtain a viscous liquid by phase inversion concentration (PIC); and (6) cooling the viscous liquid down to room temperature. The numerical values for the amounts of the components shown in Table 9 are all based on "% by weight" as active raw materials.

TABLE 9

|  | Example 6 | Comparative Example 6 |
|---|---|---|
| Polyglyceryl-5 Laurate****** (HLB: 10.9) | 5.00% | 5.00% |
| Polyglyceryl-2 Caprate*** (HLB: 9.5) | 5.00% | 5.00% |
| Isopropyl Myristate | 3.00% | 3.00% |
| Butyleneglycol | 4.00% | 4.00% |
| Phenoxyethanol | 0.50% | 0.50% |
| Caprylyl Glycol | 0.50% | 0.50% |
| 3-(2,4-Dihydroxybenzyl)1-(2-hydroxyethyl)pyrrolidine-2,5-dione | 3.00% | — |
| Water | q.s. 100% | q.s. 100% |

******SUNSOFT A-121E-C (Taiyo Kagaku)
***SUNSOFT Q-10D-C (Taiyo Kagaku)

The aspect, transparency and formation of a lamellar structure of the obtained viscous liquid according to Example 6 and Comparative Example 6 are shown in Table 10.

TABLE 10

|  | Example 6 | Comparative Example 6 |
|---|---|---|
| Aspect | Transparent | Separated Immediately |
| Transparency (%) | 86.79 | Two Phase |
| Lamellar Structure | Formed | Not Formed |

As is clear from the above results, it was found that the composition according to the present invention had a lamellar structure, and provided a more transparent or translucent aspect with better transparency, due to the presence of a resorcinol derivative in the composition.

The invention claimed is:
1. A cosmetic composition comprising:
 (a) 0.01 to 20% by weight of at least one oil, relative to the total weight of the composition;
 (b) 0.1 to 25% by weight of at least a first polyglyceryl fatty acid ester having an HLB value of at least 10.0 and a second polyglyceryl fatty acid ester having an HLB value of less than 10.0, relative to the total weight of the composition;
 (c) 0.01 to 15% by weight of at least one compound chosen from resorcinol and resorcinol derivatives, relative to the total weight of the composition; and
 (d) 50 to 99% by weight water, relative to the total weight of the composition;

wherein:
 the resorcinol derivative is selected from compounds represented by the formula (I) or a salt, a solvate, an optical isomer thereof, or a racemate thereof:

(I)

in which:
 $R_1$ independently denotes -A-B, wherein:
  A represents a single bond, a $C_1$-$C_6$ alkylene group, a $C_{6-12}$ arylene group, or a $C_{1-6}$ alkylene-$C_{6-12}$ arylene group, and
  B represents a carbocyclic group or a heterocyclic group, each of which may be substituted with at least one substituent selected from a hydroxyl group, a carboxyl group, a $C_{1-6}$ alkyl group, a $C_{1-6}$ alkylene-OH, an amino group, —$CONH_2$, —CONH—$C_{1-6}$ alkyl group, or a $C_{1-6}$ alkoxy group;
 x is an integer of 1 to 4; and
 $R_2$ and $R_3$ independently denote a hydrogen atom, a $C_{1-6}$ alkyl group, or a $C_{1-6}$ acyl group; or
 the resorcinol derivative is selected from compounds represented by the formula (II) or a salt, a solvate, an optical isomer thereof, or a racemate thereof:

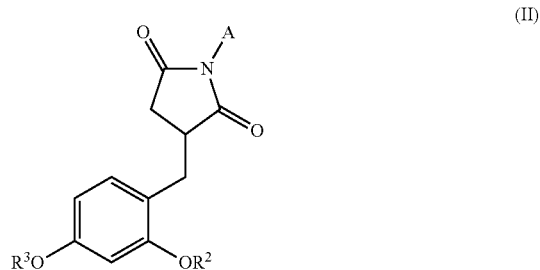

(II)

in which:
 $R_2$ and $R_3$ independently denote a hydrogen atom or an acetyl group;
 A denotes a radical selected from:
  a) —H;
  b) a $C_3$-$C_8$ cyclic or $C_3$-$C_{20}$ branched or $C_2$-$C_{20}$ unsaturated or $C_1$-$C_{20}$ saturated linear alkyl group which is optionally interrupted by one or more heteroatoms or moieties selected from N, O and —CO— or combinations thereof, and is optionally substituted by one or more identical or different groups selected from —$OR_5$ or —$SR_5$, wherein $R_5$ is selected from H and a $C_3$-$C_8$ cyclic or $C_2$-$C_{10}$ unsaturated or $C_3$-$C_{10}$ branched or $C_1$-$C_{10}$ linear saturated alkyl hydrocarbon group;

the weight ratio of the (b) at least first polyglyceryl fatty acid ester and second polyglyceryl fatty acid ester to the (a) at least one oil ranges from 1 to 10; and
the cosmetic composition has a lamellar structure.

2. The cosmetic composition according to claim 1, wherein the (b) at least first polyglyceryl fatty acid ester and second polyglyceryl fatty acid ester comprises a combination of two polyglyceryl fatty acid esters in which the HLB value of the first polyglyceryl fatty acid ester is 11.0 or more, and the HLB value of the second polyglyceryl fatty acid ester is less than 9.8.

3. The cosmetic composition according to claim 1, wherein the (b) at least first polyglyceryl fatty acid ester and second polyglyceryl fatty acid ester includes at least one of polyglyceryl monolaurate comprising 3 to 6 glycerol units, polyglyceryl mono(iso)stearate comprising 3 to 6 glycerol units, polyglyceryl monooleate comprising 3 to 6 glycerol units, or polyglyceryl monocaprate comprising 2 to 6 glycerol units.

4. The cosmetic composition according to claim 1, wherein the resorcinol derivative is a compound represented by the formula (Ia):

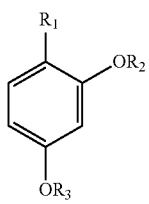

(Ia)

wherein:
$R_1$ independently denotes -A-B, where:
A represents a single bond, a $C_1$-$C_6$ alkylene group, a $C_{6-12}$ arylene group, or a $C_{1-6}$ alkylene-$C_{6-12}$ arylene group, and
B represents a carbocyclic group or a heterocyclic group, each of which may be substituted with at least one substituent selected from the group consisting of a hydroxyl group, a carboxyl group, a $C_{1-6}$ alkyl group, a $C_{1-6}$ alkylene-OH, an amino group, —$CONH_2$, —CONH—$C_{1-6}$ alkyl group, or a $C_{1-6}$ alkoxy group;
x is an integer of 1 to 4; and
$R_2$ and $R_3$ independently denote a hydrogen atom, a $C_{1-6}$ alkyl group, or a $C_{1-6}$ acyl group,
or a salt, a solvate, an optical isomer thereof, or a racemate thereof.

5. The cosmetic composition according to claim 4, wherein in the formula (Ia):
$R_1$ denotes -A-B where A represents a single bond or a $C_{1-6}$ alkylene group, and B represents a phenyl group or a tetrahydropyranyl group; and
$R_2$ and $R_3$ each denote a hydrogen atom.

6. The cosmetic composition according to claim 1, wherein, in the formula (II), $R_2$ and $R_3$ denote a hydrogen atom, and A denotes a $C_3$-$C_{10}$ branched or $C_1$-$C_{10}$ linear saturated alkyl group.

7. A method for treating skin, hair, mucous membranes, nails, eyelashes, eyebrows and/or scalp of a subject, comprising:
applying a cosmetic composition comprising:
(a) 0.01 to 20% by weight of at least one oil, relative to the total weight of the composition;

(b) 0.01 to 25% by weight of at least a first polyglyceryl fatty acid ester having an HLB value of at least 10.0 and a second polyglyceryl fatty acid ester having an HLB value of less than 10.0, relative to the total weight of the composition;
(c) 0.01 to 15% by weight of at least one compound selected from the group consisting of resorcinol and resorcinol derivatives relative to the total weight of the composition; and
(d) 50 to 99% by weight water, relative to the total weight of the composition;
wherein:
the resorcinol derivative is selected from compounds represented by the formula (I) or a salt, a solvate, an optical isomer thereof, or a racemate thereof:

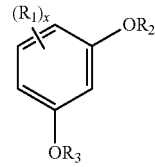

(I)

in which:
$R_1$ independently denotes -A-B wherein:
A represents a single bond, a $C_1$-$C_6$ alkylene group, a $C_{6-12}$ arylene group, or a $C_{1-6}$ alkylene-$C_{6-12}$ arylene group, and
B represents a carbocyclic group or a heterocyclic group, each of which may be substituted with at least one substituent selected from a hydroxyl group, a carboxyl group, a $C_{1-6}$ alkyl group, a $C_{1-6}$ alkylene-OH, an amino group, —$CONH_2$, —CONH—$C_{1-6}$ alkyl group, or a $C_{1-6}$ alkoxy group;
x is an integer of 1 to 4; and
$R_2$ and $R_3$ independently denote a hydrogen atom, a $C_{1-6}$ alkyl group, or a $C_{1-6}$ acyl group; or
the resorcinol derivative is selected from compounds represented by the formula (II) or a salt, a solvate, an optical isomer thereof, or a racemate thereof:

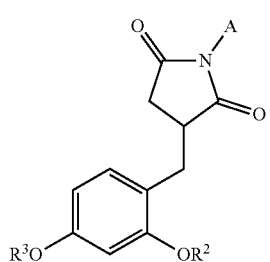

(II)

in which:
$R_2$ and Ra independently denote a hydrogen atom or an acetyl group;
A denotes a radical selected from:
a) —H:
b) a $C_3$-$C_8$ cyclic or $C_3$-$C_{20}$ branched or $C_2$-$C_{20}$ unsaturated or $C_1$-$C_{20}$ saturated linear alkyl group which is optionally interrupted by one or more heteroatoms or moieties selected from N, O and —CO— or combinations thereof, and is optionally substituted by one or more identical or different groups selected from —$OR_5$ or —$SR_5$ wherein $R_5$ is selected from H and a $C_3$-$C_8$ cyclic or $C_2$-$C_{10}$ unsaturated or $C_3$-$C_{10}$ branched or $C_1$-$C_{10}$ linear saturated alkyl hydrocarbon group;

the weight ratio of the (b) at least first polyglyceryl fatty acid ester and second polyglyceryl fatty acid ester to the (a) at least one oil ranges from 1 to 10; and the cosmetic composition has a lamellar structure to the skin, hair, mucous membranes, nails, eyelashes, eyebrows or scalp of the subject.

8. A method according to claim 7, wherein the cosmetic composition is used in or with care products, washing products, make-up products, or make-up-removing products for body, facial skin, mucous membranes, scalp, hair, nails, eyelashes, or eyebrows.

\* \* \* \* \*